United States Patent
Fife

(10) Patent No.: US 10,379,079 B2
(45) Date of Patent: Aug. 13, 2019

(54) METHODS AND APPARATUS FOR MEASURING ANALYTES USING LARGE SCALE FET ARRAYS

(71) Applicant: LIFE TECHNOLOGIES CORPORATION, Carlsbad, CA (US)

(72) Inventor: Keith G. Fife, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 78 days.

(21) Appl. No.: 14/971,435

(22) Filed: Dec. 16, 2015

(65) Prior Publication Data

US 2016/0178570 A1    Jun. 23, 2016

Related U.S. Application Data

(60) Provisional application No. 62/093,851, filed on Dec. 18, 2014.

(51) Int. Cl.
*G01N 27/414* (2006.01)

(52) U.S. Cl.
CPC ....... *G01N 27/4148* (2013.01); *G01N 27/414* (2013.01)

(58) Field of Classification Search
CPC .................................. G01N 27/4148
USPC ....................................... 257/253
See application file for complete search history.

(56) References Cited

U.S. PATENT DOCUMENTS

| | | |
|---|---|---|
| 4,086,642 A | 4/1978 | Yoshida et al. |
| 4,133,735 A * | 1/1979 | Afromowitz ...... G01N 27/3335 |
| | | 204/406 |
| 4,411,741 A | 10/1983 | Janata |
| 4,437,969 A | 3/1984 | Covington et al. |
| 4,438,354 A | 3/1984 | Haque et al. |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Litenberg et al. |
| 4,722,830 A | 2/1988 | Urie et al. |
| 4,743,954 A | 5/1988 | Brown |

(Continued)

FOREIGN PATENT DOCUMENTS

| | | |
|---|---|---|
| CN | 1582334 | 2/2005 |
| CN | 1585896 | 2/2005 |

(Continued)

OTHER PUBLICATIONS

OV5640 Datasheet Product Specification, *1/4"color CMOS QSXGA (5 megapixel) image sensor with OmniBSI technology*, May 1, 2011, p. 1, line 9 and pp. 2-7, paragraph 1.

(Continued)

*Primary Examiner* — Maris R Kessel
*Assistant Examiner* — Joshua L Allen

(57) ABSTRACT

A semiconductor device, comprising a first field effect transistor (FET) connected in series to a second FET, and a third FET connected in series to the first FET and the second FET. The semiconductor device further includes bias circuitry coupled to the first FET and the second FET, and an output conductor coupled to a terminal of the second FET, wherein the output conductor obtains an output signal from the second FET that is independent of the first FET.

12 Claims, 11 Drawing Sheets

(56) References Cited

U.S. PATENT DOCUMENTS

| | | |
|---|---|---|
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,082,788 A | 1/1992 | Farnsworth et al. |
| 5,110,441 A | 5/1992 | Kinlen et al. |
| 5,113,870 A | 5/1992 | Rossenfeld |
| 5,126,022 A | 6/1992 | Soane et al. |
| 5,126,759 A | 6/1992 | Small et al. |
| 5,132,418 A | 7/1992 | Caruthers et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,280,586 B1 | 8/2001 | Wolf et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,091,059 B2 | 8/2006 | Rhodes |
| 7,097,973 B1 | 8/2006 | Zenhausern |
| 7,105,300 B2 | 9/2006 | Parce et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,235,389 B2 | 6/2007 | Lim et al. |
| 7,238,323 B2 | 7/2007 | Knapp et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |

(56) References Cited

U.S. PATENT DOCUMENTS

| | | |
|---|---|---|
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,575,865 B2 | 8/2009 | Leamon et al. |
| 7,576,037 B2 | 8/2009 | Engelhardt et al. |
| 7,590,211 B1 | 9/2009 | Burney |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,817 B2 | 11/2009 | Tay |
| 7,614,135 B2 | 11/2009 | Santini, Jr. et al. |
| 7,622,294 B2 | 11/2009 | Walt et al. |
| 7,667,501 B2 | 2/2010 | Surendranath et al. |
| 7,733,401 B2 | 6/2010 | Takeda |
| 7,785,790 B1 | 8/2010 | Church et al. |
| 7,821,806 B2 | 10/2010 | Horiuchi |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,708 B2 | 2/2011 | Yazawa et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,072,188 B2 | 12/2011 | Yorinobu et al. |
| 8,124,936 B1 | 2/2012 | Lagna |
| 8,133,698 B2 | 3/2012 | Silver |
| 8,138,496 B2 | 3/2012 | Li et al. |
| 8,199,859 B2 | 6/2012 | Zerbe et al. |
| 8,217,433 B1 | 7/2012 | Fife |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,361,713 B2 | 1/2013 | Bridgham et al. |
| 8,415,716 B2 | 4/2013 | Rothberg et al. |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick |
| 8,653,567 B2 | 2/2014 | Fife |
| 8,658,017 B2 | 2/2014 | Rothberg et al. |
| 8,685,230 B2 | 4/2014 | Rothberg et al. |
| 8,685,298 B2 | 4/2014 | Rothberg et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,748,947 B2 | 6/2014 | Milgrew et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,841,217 B1 | 9/2014 | Fife et al. |
| 8,912,005 B1 | 12/2014 | Fife et al. |
| 8,962,366 B2 | 2/2015 | Putnam et al. |
| 8,963,216 B2 | 2/2015 | Fife et al. |
| 2002/0012933 A1 | 1/2002 | Rothberg et al. |
| 2002/0042388 A1 | 4/2002 | Cooper et al. |
| 2002/0081714 A1 | 6/2002 | Jain et al. |
| 2002/0085136 A1 | 7/2002 | Moon et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu et al. |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0155942 A1 | 8/2003 | Thewes |
| 2003/0186262 A1 | 10/2003 | Cailloux et al. |
| 2003/0211502 A1 | 11/2003 | Sauer et al. |
| 2003/0215857 A1 | 11/2003 | Kilger et al. |
| 2003/0224419 A1 | 12/2003 | Corcoran et al. |
| 2004/0002470 A1 | 1/2004 | Keith et al. |
| 2004/0023253 A1 | 2/2004 | Kunwar et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |

(56) References Cited

U.S. PATENT DOCUMENTS

| | | |
|---|---|---|
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0093645 A1 | 5/2005 | Watanabe et al. |
| 2005/0106587 A1 | 5/2005 | Klapproth et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0191698 A1 | 9/2005 | Chee et al. |
| 2005/0202582 A1 | 9/2005 | Eversmann et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0239132 A1 | 10/2005 | Klapprith |
| 2005/0282224 A1 | 12/2005 | Fouillet et al. |
| 2006/0000772 A1 | 1/2006 | Sano et al. |
| 2006/0035400 A1 | 2/2006 | Wu et al. |
| 2006/0057025 A1 | 3/2006 | Eversmann et al. |
| 2006/0057604 A1 | 3/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0047836 A1 | 2/2008 | Strand et al. |
| 2008/0096216 A1 | 4/2008 | Quake |
| 2008/0111161 A1 | 5/2008 | Sorge et al. |
| 2008/0121946 A1 | 5/2008 | Youn et al. |
| 2008/0136933 A1 | 6/2008 | Dosluoglu et al. |
| 2008/0185616 A1 | 8/2008 | Johnson et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0026082 A1 | 1/2009 | Rothberg et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127689 A1 | 5/2009 | Ye et al. |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0273386 A1 | 11/2009 | Korobeynikov et al. |
| 2010/0007326 A1 | 1/2010 | Nakazato |
| 2010/0026814 A1 | 2/2010 | Shimoda |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0244106 A1 | 9/2010 | Parker et al. |
| 2010/0273166 A1 | 10/2010 | Garcia |
| 2010/0301398 A1* | 12/2010 | Rothberg ............ G01N 27/4145 257/253 |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0217697 A1 | 9/2011 | Rothberg et al. |
| 2011/0236263 A1 | 9/2011 | Sawada et al. |
| 2011/0248320 A1 | 10/2011 | Rothberg et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001236 A1 | 1/2012 | Fife et al. |
| 2012/0001237 A1* | 1/2012 | Fife .................... G01N 27/4145 257/253 |
| 2012/0001615 A1 | 1/2012 | Levine et al. |
| 2012/0001646 A1 | 1/2012 | Bolander et al. |
| 2012/0001779 A1 | 1/2012 | Fife et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0045368 A1 | 2/2012 | Hinz et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0074956 A1* | 3/2012 | Fife .................... G01N 27/4148 324/612 |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0173159 A1 | 7/2012 | Davey et al. |
| 2012/0228136 A1 | 9/2012 | Levine |
| 2012/0261274 A1 | 10/2012 | Rearick et al. |
| 2012/0286771 A1 | 11/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329192 A1 | 12/2012 | Bustillo et al. |
| 2013/0001653 A1 | 1/2013 | Milgrew et al. |
| 2013/0009214 A1 | 1/2013 | Bustillo et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0324421 A1 | 12/2013 | Rothberg et al. |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0364320 A1 | 12/2014 | Rothberg et al. |
| 2015/0091581 A1* | 4/2015 | Sohbati ............ G01N 27/4145 324/464 |

FOREIGN PATENT DOCUMENTS

| | | |
|---|---|---|
| CN | 1703623 | 11/2005 |
| CN | 1826525 | 8/2006 |
| CN | 101669026 | 3/2010 |
| CN | 101676714 | 3/2010 |
| CN | 102203282 | 9/2011 |

(56) References Cited

FOREIGN PATENT DOCUMENTS

| | | |
|---|---|---|
| DE | 4232532 | 4/1994 |
| DE | 4430811 | 9/1995 |
| DE | 19512117 | 10/1996 |
| DE | 102008012899 | 9/2009 |
| EP | 0223618 | 5/1987 |
| EP | 1371974 | 12/2003 |
| EP | 1432818 | 6/2004 |
| EP | 1542009 | 6/2005 |
| EP | 1557884 | 7/2005 |
| EP | 1975246 | 3/2007 |
| EP | 1870703 | 12/2007 |
| EP | 2307577 | 4/2011 |
| GB | 2457851 | 9/2009 |
| GB | 2461127 B | 7/2010 |
| JP | 58070155 | 4/1983 |
| JP | 62-237349 | 10/1987 |
| JP | 02-250331 | 10/1990 |
| JP | 02-310931 | 12/1990 |
| JP | H05-080115 | 4/1993 |
| JP | 2000055874 | 2/2000 |
| JP | 2002/272463 | 9/2002 |
| JP | 2003-279532 | 10/2003 |
| JP | 2004-510125 | 4/2004 |
| JP | 2005218310 | 8/2004 |
| JP | 2005/077210 | 3/2005 |
| JP | 2005-207797 | 4/2005 |
| JP | 2005-515475 | 5/2005 |
| JP | 2006138846 | 1/2006 |
| JP | 2006-284225 | 10/2006 |
| JP | 2007/243003 | 9/2007 |
| JP | 2010513869 | 4/2010 |
| JP | 2011-525810 | 9/2011 |
| JP | 2015-506557 | 3/2012 |
| KR | 10-0442838 | 7/2004 |
| KR | 10-0455283 | 10/2004 |
| TW | 200946904 | 11/2009 |
| WO | 1989/09283 | 10/1989 |
| WO | 1998/13523 | 4/1998 |
| WO | 1998/046797 | 10/1998 |
| WO | 2001/20039 | 3/2001 |
| WO | 2001/42498 | 6/2001 |
| WO | 2001/047804 | 7/2001 |
| WO | 2001/081896 | 11/2001 |
| WO | 02/077287 | 10/2002 |
| WO | 2002/077287 | 10/2002 |
| WO | 2002/086162 | 10/2002 |
| WO | PCT/JP2003/04697 | 4/2003 |
| WO | 2003/073088 | 9/2003 |
| WO | 2004/048962 | 1/2004 |
| WO | 2004/040291 | 5/2004 |
| WO | 2005/054431 | 1/2005 |
| WO | 2005/015156 | 2/2005 |
| WO | 2005/022142 | 3/2005 |
| WO | 2005/043160 | 5/2005 |
| WO | 2005/047878 | 5/2005 |
| WO | 2005062049 | 7/2005 |
| WO | 2005/073706 | 8/2005 |
| WO | 2005/084367 | 9/2005 |
| WO | 2005/090961 | 9/2005 |
| WO | 2005090961 | 9/2005 |
| WO | 2006/005967 | 1/2006 |
| WO | 2006/056226 | 1/2006 |
| WO | 2006/022370 | 3/2006 |
| WO | 2007002204 | 1/2007 |
| WO | 2007/086935 | 8/2007 |
| WO | 2008/007716 | 1/2008 |
| WO | 2008/058282 | 5/2008 |
| WO | 2008/076406 | 6/2008 |
| WO | 2008076406 | 6/2008 |
| WO | 2008/107014 | 9/2008 |
| WO | 2009/012112 | 1/2009 |
| WO | 2009/04197 | 4/2009 |
| WO | 2009/074926 | 6/2009 |
| WO | 2009/081890 | 7/2009 |
| WO | 2009/158006 | 12/2009 |
| WO | 2010/008480 | 1/2010 |
| WO | 2010/047804 | 4/2010 |
| WO | 2010/138182 | 12/2010 |
| WO | 2010/138186 | 12/2010 |
| WO | 2010/138188 | 12/2010 |
| WO | 2012/003359 | 1/2012 |
| WO | 2012/003363 | 1/2012 |
| WO | 2012/003368 | 1/2012 |
| WO | 2012/003380 | 1/2012 |
| WO | 2012/0069222 | 1/2012 |
| WO | 2012046137 | 4/2012 |
| WO | 2012/152308 | 11/2012 |

OTHER PUBLICATIONS

International Search Report and Written Opinion of the International Searching Authority for International Application No. PCT/US2015/066052 dated Apr. 7, 2016, 19 pages.
International Search Report and Written Opinion of the International Searching Authority for International Application No. PCT/US2015/066110 dated Mar. 17, 2016, 14 pages.
Terada, Kazuo et al., "Further Study of Vth-Mismatch Evaluation Circuit", *Proceedings of IEEE 2004 Int. Conference on Microelectronic Test Structures*, vol. 17. Mar. 22, 2004, pp. 155-159.
[No Author Listed], "ISFET Wikipedia article", *Wikipedia*, Last modified Nov. 7, 2006, 2006.
Ahmadian, et al., "Single-nucleotide polymorphism analysis by pyrosequencing", *Anal. Biochem*, vol. 280, 2000, 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767, , "Search Information Statement", Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M. et al., "Fully electronic DNA hybridization detection by a standard CMOS biochip", *Sensors and Actuators B Chemical, vol. 118*, 2006, 41-46.
Bashford, G. et al., "Automated bead-trapping apparatus and control system for single-molecule DNA sequencing", *Optics Express*, vol. 16(5), Mar. 3, 2008, pp. 3445-3455.
Baumann, W. et al., "Microelectronic sensor system for microphysiological application on living cells", *Sensors Actuators B*, vol. 55, 1999, pp. 77-89.
Bausells, J. et al., "Ion-sensitive field-effect transistors fabricated in a commercial CMOS technology", *Sensors and Actuators B Chemical*, vol. 57, 1999, pp. 56-62.
Bergveld, , "ISFET, Theory and Practice", *IEEE Sensor Conference, Toronto*, Oct. 2003, 2003, pp. 1-26.
Bergveld, , "Thirty years of ISFETOLOGY What happened in the past 30 years and what may happen in the next 30 years", *Sensors and Actuators B*, vol. 88, 2003, pp. 1-20.
Besselink, et al., "ISFET Affinity Sensor", *Methods in Biotechnology, vol. 7: Affinity Biosensors: Techniques and Protocols*, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.
Bockelmann, U. et al., "Detecting DNA by field effect transistor arrays", *Proceedings of the 2006 IFIP International Conference on Very Large Scale Integration*. 2006, 164-168.
Bousse, L. et al., "A process for the combined fabrication of ion sensors and CMOS circuits", *IEEE Electron Device Letters*, vol. 9(1), 1988, pp. 44-46.

(56) References Cited

OTHER PUBLICATIONS

Bousse, L. et al., "Zeta potential measurements of Ta2O5 and SiO2 thin films", *J. Colloid Interface Sci.*, vol. 147(1), 1991, pp. 22-32.
Chan, Wai P. et al., "An Integrated ISFETs Instrumentation System in Standard CMOS Technology", *IEEE Journal of Solid-State Circuits, vol. 45, No. 9*, Sep. 2010, pp. 1923-1934.
Chen, Y. et al., "Nanoscale field effect transistor for biomolecular signal amplification", *App Phys Letter*, vol. 91, 2007, pp. 243511-1-243511-3.
Chen, Y. et al., "Silicon-based nanoelectronic field-effect pH sensor with local gate control", *App Phys Letter*, vol. 89, 2006, pp. 223512-1-223512-3.
Chin, Yuan-Lung et al., "Titanium Nitride Membrane Application to Extended Gate Field Effect Transistor pH Sensor Using VLSI Technology", *Jpn. J. Appl. Phys. vol. 40, Part 1, No. 11*, Nov. 2001, pp. 6311-6315.
Chou, J. et al., Letter to the Editor on "Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-76.
Chung, et al., "ISFET interface circuit embedded with noise rejection capability", *Electronics Letters*, vol. 40, No. 18, Oct. 2004, 1115-1116.
Chung, W-Y et al., "ISFET performance enhancement by using the improved circuit techniques", *Sensors and Actuators B*, vol. 113, 2006, pp. 555-562.
Chung, W-Y et al., "New ISFET interface circuit design with temperature compensation", *Microelectronics Journal*, vol. 37(10), Oct. 1, 2006, pp. 1105-1114.
Chung, W-Y et al., "Temperature compensation electronics for ISFET readout applications", *Biomedical Circuits and Systems*, IEEE International Workshop Singapore, Dec. 1, 2004, pp. 305-308.
Dazhong, Z. et al., "Research of CMOS Biosensor IC for Extracellular Electrophysiological Signal Recording and pH value Measuring", *Solid-State and Integrated-Circuit Technology, 9th International Conference*, NJ USA, Oct. 20, 2008, pp. 2557-2560.
Dorf, Richard C., "The Electrical Engineering Handbook", *University of California, Davis, CRC Press, 2 edition, Chapter 3—Linear Circuit Analysis*, Jun. 25, 2004, pp. 3-1 to 3-66.
Eijkel, J. et al., "Measuring Donnan-related phenomena using a solid-state ion sensor and a concentration-step method", *J. Membrane Sci.*, vol. 127, 1997, pp. 203-221.
Eijkel, J., "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662.
EP09798251.6, "Extend European Search Report" dated Aug. 27, 2013, 6 pages.
EP09822323.3, "European Extended Search Report" dated May 27, 2015, 8 pages.
EP10780930, "European Search Report" dated Jun. 15, 2015, 3 pages.
EP10857377, "European Search Report" dated Jun. 26, 2015, 3 pages.
EP11801437.2, "European Extended Search Report" dated Jul. 25, 2013, 10 pages.
EP11801437.2, "LT00349EP Examination Notification" dated Feb. 12, 2015, 8 pages.
EP11801439.8, "Extended Search Report" dated Mar. 7, 2014, 9 pages.
EP11804218.3, "European Extended Search Report" dated Jul. 11, 2013, 3 pages.
EP11827128.7, "European Search Report" dated Aug. 1, 2013, 5 pages.
EP13161312.7, "Extend European Search Report" dated Oct. 15, 2013, 8 pages.
EP13163995.7, "EP Search Report" dated Jul. 9, 2014.
EP13163995.7, "Extend European Search Report" dated Aug. 20, 2013, 6 pages.
EP13164768.7, "European Search Report" dated Aug. 20, 2013, 6 pages.
EP13174555.6, "EP Extended Search Report" dated Dec. 12, 2013, 8 pages.
EP13174555.6, "EP Search Report" dated Nov. 21, 2013, 5 pages.
EP13177039.8, "EP Search Report" dated Nov. 21, 2013, 9 pages.
EP13177590.0, "EP Search Report" dated Nov. 20, 2013, 5 pages.
EP13177590.0, "European Examination Notification" dated Sep. 8, 2014, 9 pages.
EP14152861.2, "EP Search Report" dated Jul. 7, 2014, 5 pages.
EP7867780.4, "Examination Report" dated Jul. 3, 2012.
Eriksson, J. et al., "Pyrosequencing technology at elevated temperature", *Electrophoresis*, vol. 25, 2004, pp. 20-27.
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.
Eversmann, B. et al., "A 128 × 128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J., "Handbook of Modern Sensors—Physics, Designs, and Applications . . .", *17.3.2 CHEMFET Sensors*, 1996, pp. 499-501.
Fritz, J. et al., "Electronic detection of DNA by its intrinsic molecular charge", *PNAS*, vol. 99, No. 22, Oct. 2002, 14142-14146.
Gardner, J.W. et al., "Enhancing electronic nose performance by sensor selection using a new integer-based genetic algorithm approach", *Science Direct, Sensors and Actuators B*, vol. 106, 2005, pp. 114-121.
GB0811656.8, "Search and Examination Report" dated Mar. 12, 2010.
GB0811656.8, "Search Report" dated Sep. 21, 2009.
GB0811657.6, "Examination Report" dated Jun. 30, 2010.
GB0811657.6, "Search Report under Section 17" dated Oct. 26, 2009.
Gracia, I. et al., "Test Structures for ISFET Chemical Sensors", *Proc IEEE 1992 Intl Conf Microelec Test Struct*, vol. 5, 1992, pp. 156-159.
Hammond, et al., "Performance and system-on-chip integration of an unmodified CMOS ISFET", *Science Direct, Sensors and Actuators vol. 111-112*, 2005, pp. 254-258.
Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P. et al., "Design of a Single-Chip pH Sensor Using a Conventional 0.6-μm CMOS Process", *IEEE Sensors Journal*, vol. 4(6), 2004, 706-712.
Hammond, P. et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hamster ovary cell line using Illumina sequencing technology", *BMC Genomics*, vol. 12:67, 2011, pp. 1-8.
Han, Y, "Label-free detection of biomolecules by a field-effect transistor microarray biosensor with bio-functionalized gate surfaces", Masters Dissertation, 2006, pp. 1-63.
Hanshaw, R. et al., "An indicator displacement system for fluorescent detection of phosphate oxyanions under physiological conditions", *Science Direct, Tetrahedron Letters*, vol. 45, Nov. 15, 2004, pp. 8721-8724.

(56) References Cited

OTHER PUBLICATIONS

Hara, H. et al., "Dynamic response of a Ta2O5-gate pH-sensitive field-effect transistor", Sensors Actuators B, vol. 32, 1996, pp. 115-119.
Hermon, Z. et al., "Miniaturized bio-electronic hybrid for chemical sensing applications", Tech Connect News, Apr. 22, 2008, pp. 1.
Hideshima, S. et al., "Detection of tumor marker in blood serum using antibody-modified field effect transistor with optimized BSA blocking", Sensors and Actuations B: Chemical, vol. 161, 2012, pp. 146-150.
Hijikata, et al., "Identification of a Single Nucleotide Polymorphism in the MXA Gene Promoter (T/T at nt-88) Correlated with the Response of Hepatitis C Patients to Interferon", Intervirology, vol. 43, 2000, 124-127.
Hizawa, et al., "Sensing Characteristics of Charge Transfer Type pH Sensor by Accumulative Operation", IEEE Sensors. EXCO, Daegu, Korea, Oct. 22-25, 2006, pp. 144-147.
Hizawa, T et al., "Fabrication of a two-dimensional pH image sensor using a charge transfer technique", Sensors and Actuators B Chemical, vol. 117, 2006, 509-515.
Hizawa, T. et al., "32 ×32 pH Image Sensors for Real Time Observation of Biochemical Phenomena", Transducers & Eurosensors '07, 14th Intl. Conf. on Solid-State, Actuators and Microsystems, Lyon, France, Jun. 10-14, 2007, 2007, pp. 1311-1312.
Ingebrandt, Sven et al., "Label-free detection of DNA using field-effect transistors", Phys. stat. sol. (a) 203, No. 14, 2006, pp. 3399-3411.
Jakobson, C. et al., "Low frequency noise and drift in Ion Senstive Field Effect Transistors", Sensors Actuators B, vol. 68, 2000, pp. 134-139.
Ji, H. et al., "A CMOS contact imager for locating individual cells", ISCAS, 2006, pp. 3357-3360.
Ji, H. et al., "Contact Imaging: Simulation and Experiment", IEEE Trans Circuits Systems-I: Regular Papers, vol. 54(8), 2007, pp. 1698-1710.
Kim, D. et al., "An FET-type charger sensor for highly sensitive detection of DNA sequence", Biosens Bioelectron, vol. 20(1), 2004, pp. 69-74.
Klein, M. , "Time effects of ion-sensitive field-effect transistors", Sens Act B, vol. 17, 1989, pp. 203-208.
Koch, S et al., "Protein detection with a novel ISFET-based zeta potential analyzer", Biosensors & Bioelectronics, vol. 14, 1999, pp. 413-421.
Krause, M. et al., "Extended gate electrode arrays for extracellular signal recordings", Sensors and Actuators B, vol. 70, 2000, pp. 101-107.
Kruise, J. et al., "Detection of protein concentrations using a pH-step titration method", Sensors Actuators B, vol. 44, 1997, pp. 297-303.
Leamon, J. et al., "A Massively Parallel PicoTiterPlate Based Platform for Discrete Picoliter-Scale Polymerase Chain Reactions", Electrophoresis, vol. 24, 2003, pp. 3769-3777.
Leamon, J. et al., "Cramming More Sequencing Reactions onto Microreactor Chips", Chemical Reviews, vol. 107, 2007, pp. 3367-3376.
Lee, C-S et al., "Ion-sensitive Field-Effect Transistor for Biological Sensing", Sensors, vol. 9, 2009, pp. 7111-7131.
Lee, S. et al., "An Enhanced Glucose Biosensor Using Charge Transfer Techniques", Biosensors and Bioelectronics, vol. 24, 2008, pp. 650-656.
Li, et al., "Sequence-Specific Label-Free DNA Sensors Based on Silico Nanowires", Nano Letters,, vol. 4, No. 2, 2004, 245-247.
Lin, B.J. et al., "Practicing the Novolac deep-UV portable conformable masking technique", Journal of Vacuum Science and Technology, Vo. 19, No. 4, 1981, 1313-1319.
Lohrengel, M. et al., "A new microcell or microreactor for material surface investigations at large current densities", Electrochimica Acta, vol. 49, 2004, pp. 2863-2870.
Lui, A. et al., "A Test Chip for ISFET/CMNOS Technology Development", Proc. of the 1996 IEEE Intl. Conf. on Microelectronic Test Structures, vol. 9, 1996, pp. 123-128.
Maki, W et al., "Nanowire-transistor based ultra-sensitive DNA methylation detection", Biosensors & Bioelectronics, 23, 2008, pp. 780-787.
Margulies, et al., "Genome sequencing in microfabricated high-density picolitre reactors", Nature, vol. 437 (15), Jul. 31, 2005, 376-380.
Marshall, et al., "DNA chips: an array of possibilities", Nature Biotechnology, vol. 16, 1998, 27-31.
Martinoia, S. et al., "A behavioral macromodel of the ISFET in SPICE", Sensors Actuators B, vol. 62, 2000, pp. 182-189.
Martinoia, S. et al., "Development of ISFET Array-Based Microsystems for Bioelectrochemical measurements of cell populations", Biosensors & Bioelectronics, vol. 16, 2001, pp. 1043-1050.
Matsuo, J. et al., "Charge Transfer Type pH Sensor with Super High Sensitivity", the 14th international conference on solid-state sensors actuators and microsystems, France, Jun. 10-14, 2007, pp. 1881-1884.
Medoro, G. et al., "A Lab-on-a-Chip for Cell Detection and Manipulation", IEEE Sensors J, vol. 3(3), 2003, pp. 317-325.
Meyburg, et al., "N-Channel field-effect transistors with floating gates for extracellular recordings", Biosens Bioelectron, vol. 21(7), 2006, pp. 1037-1044.
Milgrew, et al., "The fabrication of scalable multi-sensor arrays using standard CMOS technology", 2003 IEEE Custom Integrated Circuits Conference, 2003, pp. 513-516.
Milgrew, M. et al., "A 16 ×16 CMOS proton camera array for direct extracellular imaging of hydrogen-ion activity", IEEE Intl Solid-State Circuits Conf, Session 32:24, 2008, pp. 590-591;638.
Milgrew, M. et al., "A large transistor based sensor array chip for direct extracellular imaging", Sensors and Actuators B Chemical, vol. 111-112, 2005, 347-353.
Milgrew, M. et al., "Matching the transconductance characteristics of CMOS ESFET arrays by removing trapped charge", IEEE Trans Electron Devices, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", Sensors and Actuators B, vol. 103, 2004, 37-42.
Milgrew, M.J. et al., "The development of scalable sensor arrays using standard CMOS technology", ScienceDirect, Sensors and Actuators, vol. 103, 2004, pp. 37-42.
Milgrew, Mark J. et al., "A Proton Camera Array Technology for Direct Extracellular Ion Imaging", IEEE International Symposium on Industrial Electronics. 2008, 2051-2055.
Miyahara, Y. et al., "Biochip Using Micromachining Technology", J. Institute of Electrostatics, Japan, vol. 27, No. 6, 2003, 268-272.
Miyahara, Y. et al., "Direct Transduction of Primer Extension into Electrical Signal Using Genetic Field Effect Transistor", Micro Total Analysis Systems 2004, vol. 1, 2004, pp. 303-305.
Miyahara, Y. et al., "Potentiometric Detection of DNA Molecules Using Field Effect Transistor", The Japan Society of Applied Physics, No. 3 (Translation included), 2003, 1180, 30A-S2.
Naidu, M. S. et al., "Introduction to Electrical Engineering", Chapter 1—Fundamental Concepts of Electricity, McGraw Hill Education (India) Private Limited, 1995, pp. 1-10.
Neaman, Donald A. , "Electronic Circuit Analysis and Design", McGraw Hill Higher Education, 2nd edition, Chapter 6—Basic FET Amplifiers, (reference will be uploaded in 2 parts due to size) part 1 of 2, Dec. 1, 2000, pp. 313-345.
Neaman, Donald A. , "Electronic Circuit Analysis and Design", McGraw Hill Higher Education, 2nd edition, Chapter 6—Basic FET Amplifiers, (reference will be uploaded in 2 parts due to size) part 2 of 2, Dec. 1, 2000, pp. 346-381.
Nishiguchi, K. et al., "Si nanowire ion-sensitive field-effect transistors with a shared floating gate", Applied Physics Letters vol. 94, 2009, pp. 163106-1 to 163106-3.
Nyren, P. et al., "Enzymatic Method for Continuous Monitoring of Inorganic Pyrophosphate Synthesis", Analytical Biochemistry, vol. 151, 1985, pp. 504-509.

(56) References Cited

OTHER PUBLICATIONS

Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Palan, B. et al., "New ISFET sensor interface circuit for biomedical applications", *Sensors and Actuators B: Chemical: International Journal Devoted to Research and Development of Physical and Chemical Transducers, Elsevier S.A. Ch.*, vol. 57, No. 1-3, 1999, pp. 63-68.
Park, K-Y et al., "ISFET glucose sensor system with fast recovery characteristics by employing electrolysis", *Sensors and Actuators B: Chemical*, vol. 83 (1-3), Mar. 15, 2002, pp. 90-97.
Patolsky, F. et al., "Nanowire-Based Biosensors", *Analyt Chem 1*, vol. 78(13), 2006, pp. 4261-4269.
PCT/JP2005/001987, "International Search Report" dated Apr. 5, 2005.
PCT/JP2005/015522, "International Preliminary Report on Patentability" dated Mar. 19, 2007.
PCT/JP2005/015522, "International Search Report" (includes English translation) dated Sep. 27, 2005.
PCT/US/2009/05745, "International Preliminary Report on Patentability" dated Apr. 26, 2011.
PCT/US/2009/05745, "International Search Report and Written Opinion" dated Dec. 11, 2009.
PCT/US2007/025721, "Declaration of Non-Establishment of International Search Report" dated Jul. 15, 2008.
PCT/US2007/025721, "International Preliminary Report on Patentability" dated Jun. 16, 2009.
PCT/US2007/025721, "Written Opinion" dated Jun. 16, 2009.
PCT/US2009/003766, "International Preliminary Report on Patentability" dated Jan. 5, 2011.
PCT/US2009/003766, "International Search Report and Written Opinion" dated Apr. 8, 2010.
PCT/US2009/003797, "International Search Report and Written Opinion" dated Mar. 12, 2010.
PCT/US2010/001543, "International Preliminary Report on Patentability" dated Nov. 29, 2011, pp. 1-8.
PCT/US2010/001543, "International Search Report and Written Opinion" dated Oct. 13, 2010, pp. 1-12.
PCT/US2010/001553, "International Preliminary Report on Patentability" dated Dec. 8, 2011, pp. 1-10.
PCT/US2010/001553, "International Search Report and Written Opinion" dated Jul. 28, 2010, pp. 1-2.
PCT/US2010/048835, "International Preliminary Report on Patentability" dated Mar. 19, 2013, 7 pages.
PCT/US2010/48835, "International Search Report and Written Opinion" dated Dec. 16, 2010, pp. 1-12.
PCT/US2011/042655, "International Search Report" dated Oct. 21, 2011, pp. 1-2.
PCT/US2011/042660, "International Search Report" dated Nov. 2, 2011.
PCT/US2011/042665, "International Search Report" dated Nov. 2, 2011.
PCT/US2011/042668, "International Preliminary Report on Patentability" dated Mar. 26, 2013, 11 pages.
PCT/US2011/042668, "International Search Report" dated Oct. 28, 2011.
PCT/US2011/042669, "International Search Report and Written Opinion" dated Jan. 9, 2012, pp. 1-5.
PCT/US2011/042683, "International Preliminary Report on Patentability" dated Jun. 4, 2013, 5 pages.
PCT/US2011/042683, "International Search Report and Written Opinion" dated Feb. 16, 2012.
PCT/US2012/058996, "International Search Report and Written Opinion" dated Jan. 22, 2013, pp. 1-11.
PCT/US2012/071471, "International Preliminary Report on Patentability" dated Jun. 24, 2014, 8 pages.
PCT/US2012/071471, "International Search Report of the International Searching Authority and Written Opinion" dated Apr. 24, 2013, 14 pages.
PCT/US2012/071482, "International Preliminary Amendment" dated Jun. 24, 2014, 7 pages.
PCT/US2012/071482, "International Search Report of the International Searching Authority and Written Opinion" dated May 23, 2013, 11 pages.
PCT/US2013/022129, "International Preliminary Report on Patentability" dated Jul. 22, 2014, 11 pages.
PCT/US2013/022129, "International Search Report of the International Searching Authority and Written Opinion" dated Aug. 9, 2013, 18 pages.
PCT/US2013/022140, "International Preliminary Report on Patentability" dated Jul. 22, 2014, 9 pages.
PCT/US2013/022140, "International Search Report of the International Searching Authority and Written Opinion" dated May 2, 2013, 15 pages.
PCT/US2014/020887, "International Preliminary Report on Patentability" dated Sep. 15, 2015, 8 pages.
PCT/US2014/020887, "International Search Report and Written Opinion" dated May 30, 2014, 12 pages.
PCT/US2014/020892, "International Search Report and Written Opinion" dated Jun. 3, 2014.
PCT/US2014/040923, "International Search Report and Written Opinion" dated Sep. 1, 2014, 14 pages.
Poghossian, A. et al., "Functional testing and characterization of ISFETs on wafer level by means of a micro-droplet cell", *Sensors*, vol. 6, 2006, pp. 397-404.
Pollack, J. et al., "Genome-wide analysis of DNA copy-numbe changes using cDNA microarrays", *Nature Genetics, Nature America Inc.*, vol. 23, Sep. 1999, pp. 41-46.
Pourmand, N. et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, et al., "Ultra-low power precision ISFET readout using global current feedback", *Electronic Letters*, vol. 42, No. 22, Oct. 2006, 1264-1265.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Drift Reduction in Ion-Sensitive FETs using correlated double sampling", *Electronics Letters*, vol. 43, No. 16, Aug. 2, 2007, 857 (2 pages).
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968.
Purushothaman, S. et al., "Towards Fast Solid State DNA Sequencing", *IEEE ISCAS 2002 Proceedings*, Circuits and Systems, vol. 4, 2002, pp. IV-169-IV-172.
Rodriguez-Villegas, E., "Solution to trapped charge in FGMOS transistors", *Electronics Letters*, vol. 39(19), 2003.
Ronaghi, M. et al., "A Sequencing Method Based on Real-Time Pyrophosphate", *Science*, vol. 281, 1998, 363-365.
Rothberg, J. et al., "An integrated semiconductor device enabling non-optical genome sequencing", *Nature, vol. 475, No. 7356*, Jul. 21, 2011, pp. 348-352.
Sakata, et al., "Potentiometric Detection of DNA Using Genetic Transistor", *Denki Gakkai Kenkyukai Shiryo Chemical Sensor Kenkyukai*, CHS-03-51-55, 2003, 1-5.

(56) References Cited

OTHER PUBLICATIONS

Sakata, T. et al., "Cell-based field effect devices fo cell adhesion analysis", *Intl. Conf. on Microtechnologies in Medicine and Biology, May 9-12, 2006, Okinawa, Japan*, 2006, pp. 177-179.
Sakata, T. et al., "Detection of DNA recognition events using multi-well field effect transistor", *Biosensors and Bioelectronics vol. 21*, 2005, pp. 827-832.
Sakata, T. et al., "Detection sensitivity of genetic field effect transistor combined with charged nanoparticle-DNA conjugate", *Proc. of 2006 Intl. Conf. on Microtechnologies in Medicine and Biology, May 9-12, 2005, Okinawa, Japan*, 2006, pp. 97-100.
Sakata, T. et al., "Direct detection of single nucleotide polymorphism using genetic field effect transistor", *Digest of Papers Microprocesses and Nanotechnology 2004, Osaka, Japan*, 2004 International Microprocesses and Nanotechnology Conference, 2004, pp. 226-227.
Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology, Kahuku, Oahu, HI, May 12-15, 2005*, 2005, pp. 219-222.
Sakata, T. et al., "Direct transduction of allele-specific primer extension into electrical signal using genetic field effect transistor", *Biosensors and Bioelectronics*, vol. 22, 2007, pp. 1311-1316.
Sakata, T. et al., "DNA Analysis Chip Based on Field-Effect Transistors", *Japanese Journal of Applied Physics*, vol. 44(4B), 2005, pp. 2854-2859.
Sakata, T. et al., "DNA Sequencing Based on Intrinsic Molecular Charges", *Angewandte Chemie International Edition 2006*, vol. 118, 2006, 2283-2286.
Sakata, T. et al., "DNA Sequencing Based on Intrinsic Molecular Charges", *Angewandte Chemie International Edition 2006*, vol. 45, 2006, pp. 2225-2228.
Sakata, T. et al., "DNA Sequencing Using Genetic Field Effect Transistor", *13th Intl. Conf. on Solid-State Sensors, Actuators and Microsystems, Jun. 5-9, 2005, Seoul, Korea*, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.
Sakata, T. et al., "Potential Response of Genetic Field Effect Transistor to Charged Nanoparticle-DNA Conjugate", *Digest of Papers Microprocesses and Nanotechnology 2005, Tokyo, Japan*, 2005 Intl Microprocesses and Nanotech Conference, Hotel Bellclassic, 2005, pp. 42-43.
Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.
Sakata, T. et al., "Potentiometric Detection of Single Nucleotide Polymorphism by Using a Genetic Field-effect transistor", *ChemBioChem*, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", Thesis, Presented at Stanford University, 2005, pp. ii-78.
Salama, K., "Modeling and simulation of luminescence detection platforms", *Biosensors & Bioelectronics*, 2004, pp. 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, R. et al., "A new approach to immunoFET operation", *Biosensors & Bioelectronics*, vol. 5, 1990, pp. 103-124.
Schasfoort, R. et al., "Field-effect flow control for microfabricated fluidic networks", *Science*, vol. 286(5441), 1999, pp. 942-945.
Schoning, M. et al., "Bio FEDs (Field-Effect Devices): State-of-the-Art and New Directions", *Electroanalysis*, vol. 18(19-20), 2006, pp. 1893-1900.
Seong-Jin, K. et al., "Label-Free CMOS DNA Quantification With On-Chip Noise Reduction Schemes", *Solid-State Sensors, Actuators and Microsystems Conference, IEEE*, Jun. 10, 2013, pp. 947-950.
SG200903992-6, , "Search and Examination Report (Favourable) dated Jan. 20, 2011", 12.
Shah, N., "Microfabrication of a parellel-array DNA pyrosequencing chip", NNIN REU Research Accomplishments, 2005, pp. 130-131.
Shepherd, L. et al., "A biochemical translinear principle with weak inversion ISFETs", *IEEE Trans Circuits Syst-I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .*, 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, 5354-5361.
Simonian, A. L. et al., "FET based biosensors for the direct detection of organophosphate neurotoxins", *Electroanalysis*, vol. 16(22), 2004, pp. 1896-1906.
Souteyrand, E. et al., "Direct detection of the hybridization of synthetic homo-oligomer DNA sequences by field effect", *J Phys Chem B*, vol. 101(15), 1997, pp. 2980-2985.
Starodub, N. et al., "Immunosensor for the determination of the herbicide simazine based on an ion-selective field-effect transistor", *Analytica Chimica Acta*, vol. 424, 2000, pp. 37-43.
Takenaka, et al., "DNA Sensing on a DNA Probe-Modified Electrode Using Ferrocenylnaphthalene Dimide as the Electrochemically Active Ligand", *Anal. Chem.*, vol. 72, No. 6, 2000, 1334-1341.
Temes, G.C. et al., "A Tutorial Discussion of The Oversampling Method for A/D and D/A Conversion", *1990 IEEE International Symposium on circuits and Systems*, vol. 2 of 4, 1990, 5 pages.
Thewes, R. et al., "CMOS-based Biosencor Arrays", *Proceedings of the Design, Automation and Test in Europe Conference and Exhibition*, 2005, 2 pages.
Tokuda, T. et al., "A CMOS image sensor with optical and potential dual imaging function for on-chip bioscientific applications", *Sensors and Actuators A*, vol. 125, No. 2, 2006, 273-280.
Tomaszewski, D. et al., "Electrical characterization of ISFETs", *J Telecomm Info Technol*, Mar. 2007, pp. 55-60.
Toumazou, C. et al., "Using transistors to linearase biochemistry", *Electronics Letters*, vol. 43(2), Jan. 18, 2007, 3 pages.
Truman, P., "Monitoring liquid transport and chemical composition in lab on . . .", *Lab on a Chip*, vol. 6, 2006, pp. 1220-1228.
Uslu, F. et al., "Labelfree fully electronic nucleic acid detection system based on a field-effect transistor device", *Biosens & Bioelectron*, vol. 19(12), 2004, pp. 1723-1731.
Van Der Schoot, Bart et al., "The Use of a Multi-ISFET Sensor Fabricated in a Single Substrate", *Letter to the Editors, Sensors and Actuators*, vol. 12, 1987, pp. 463-468.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.

(56) References Cited

OTHER PUBLICATIONS

Van Kerkhof, , "The Development of an ISFET based heparin sensor using the ion-step measuring method", *Biosensors and Bioelectronics*, vol. 9, Nos. 9-10, 1993, 463-472.
Van Kerkhof, "The Development of an ISFET-based Heparin Sensor", *Thesis*, 1994.
Van Kerkhof, J et al., "The ISFET based heparin sensor with a monolayer of protamine as affinity ligand", *Biosensors & Bioelectronics*, vol. 10(3), 1995, pp. 269-282.
Van Kerkhof, J. et al., "ISFET Responses on a stepwise change in electrolyte concentration at constant pH", *Sensors Actuators B: Chemical*, vol. 18-19, 1994, pp. 56-59.
Vardalas, John , "Twists and Turns in the Development of the Transistor", *IEEE-USA Today's Engineer Online*, May 2003, 6 pages.
Voigt, H. et al., "Diamond-like carbon-gate pH-ISFET", *Sensors and Actuators B.*, vol. 44, 1997, pp. 441-445.
Wagner, T et al., "'All-in-one' solid-state device based on a light-addressable potentiometric sensor platform", *Sensors and Actuators B*, vol. 117, 2006, pp. 472-479.
Wang, W. et al., "Label-free detection of small-molecule-protein interactions by using nanowire nanosensors", *Proc. of the Natl. Acad.of Sciences (PNAS)*, vol. 102(9), 2005, pp. 3208-3212.
Wilhelm, D. et al., "pH Sensor Based on Differential Measurements on One pH-FET Chip", *Sensors and Actuators B*, vol. 4, 1991, pp. 145-149.
Woias, P , "Modelling the short time response of ISFET sensors", *Sensors and Actuators B*, vol. 24-25, 1995, pp. 211-217.
Woias, P. et al., "Slow pH response effects of silicon nitride ISFET sensors", *Sensors and Actuators B*, vol. 48, 1998, pp. 501-504.
Wood, et al., "Base composition-independent hybridization in tetramethylammonium chloride: a method for oligonucleotide screening of highly complex gene libraries", *Proceedings of the National Academy of Sciences*, vol. 82, 1985, 1585-1588.
Wu, P. et al., "DNA and protein microarray printing on silicon nitride waveguide surfaces", *Biosensens Bioelectron*, vol. 21(7), 2006, pp. 1252-1263.
Xu, J-J et al., "Analytical Aspects of FET-Based Biosensors", *Frontiers in Bioscience*, vol. 10, 2005, pp. 420-430.
Yeow, T.C.W. et al., "A very large integrated pH-ISFET sensor array chip compatible with standard CMOS processes", *Sensor and Actuators B*, vol. 44, 1997, 434-440.
Yoshida, Shoji et al., "Development of a Wide Range pH Sensor based on Electrolyte-Insulator-Semiconductor Structure with Corrosion-Resistant Al2O3—Ta2O5 and Al2O3—ZrO2", *Journal of the Electrochemical Society* vol. 151(3), 2004, pp. H53-H58.
Yuqing, M. et al., "Ion sensitive field effect trnasducer-based biosensors", *Biotechnology Advances*, vol. 21, 2003, pp. 527-534.
Zhang, X. et al., "32-Channel Full Customized CMOS Biosensor Chip for Extracellular neural Signal Recording", *Proc. of the 2nd Intl. IEEE EMBs Conf. on Neural Engineering, Arlington, Virginia*, 2005, pp. v-viii.
Zhao, B. et al., "Floating-Gate Ion Sensitive Field-Effect Transistor for Chemical and Biological Sensing", *MRS Proceedings, vol. 828*, 2005, pp. 349-354.
Zhou, et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, 1-11.
PCT/US2015/066052, International Preliminary Reporrt on Patentability, dated Jun. 29, 2017, 1-16.
PCT/US2015/066110, International Preliminary Report on Patentability, dated Jun. 20, 2017, 1-8.

\* cited by examiner

METHODS AND APPARATUS FOR MEASURING ANALYTES USING LARGE SCALE FET ARRAYS

CROSS-REFERENCE TO RELATED APPLICATIONS

This application claims priority to U.S. Provisional Application No. 62/093,851 filed Dec. 18, 2014, the entire contents of which is incorporated by reference herein in its entirety.

FIELD OF THE INVENTION

This disclosure, in general, relates to semiconductor devices and/or sensors for chemical analysis, and to methods for manufacturing such semiconductor devices and/or sensors.

BACKGROUND

A variety of types of sensors have been used in the detection of chemical and/or biological processes. One type is a chemically-sensitive field effect transistor (chemFET). A chemFET includes a gate, a source, a drain separated by a channel region, and a sensitive area, such as a surface on the gate adapted for contact with a fluid, coupled to the channel region. The operation of the chemFET is based on the modulation of channel conductance caused by changes, such as changes in voltage, at the sensitive area which can be due to a chemical and/or biological reaction occurring in the fluid, for example. The modulation of the channel conductance can be sensed to detect and/or determine characteristics of the chemical and/or biological reaction that cause changes at the sensitive area. One way to measure the channel conductance is to apply appropriate bias voltages to the source and drain, and measure a resulting current flowing through the chemFET. A method of measuring channel conductance can include driving a known current through the chemFET and measuring a resulting voltage at the source or drain.

An ion-sensitive field effect transistor (ISFET) is a type of chemFET that includes an ion-sensitive layer at the sensitive area. The presence of ions in a fluid containing an analyte alters the surface potential at the interface between the ion-sensitive layer and the analyte fluid which can be due to the protonation or deprotonation of surface charge groups caused by the ions present in the fluid (i.e. an analyte solution). The change in surface potential at the sensitive area of the ISFET affects the gate voltage of the device, and thereby channel conductance, which change can be measured to indicate the presence and/or concentration of ions within the solution. Arrays of ISFETs can be used for monitoring chemical and/or biological reactions, such as DNA sequencing reactions based on the detection of ions present, generated, or used during the reactions. (See, for example, U.S. Pat. No. 7,948,015 to Rothberg et al., which is incorporated by reference herein in its entirety.) More generally, large arrays of chemFETs or other types of sensors and detectors can be employed to detect and measure static and/or dynamic amounts or concentrations of a variety of analytes in a variety of processes. For example, the processes can be chemical and/or biological reactions, cell or tissue cultures or monitoring neural activity, nucleic acid sequencing, etc.

SUMMARY

In one exemplary embodiment, a semiconductor device is disclosed. The semiconductor device includes a first field effect transistor (FET) connected in series to a second FET, a third FET connected in series to the first FET and the second FET, bias circuitry coupled to the first FET and the second FET, and an output conductor coupled to a conduction terminal of the second FET, wherein the output conductor obtains an output signal from the second FET that is independent of the first FET. In some embodiments, the third FET concurrently couples the first FET and the second FET to the output conductor in response to a select signal. In some embodiments, the output signal from the second FET is independent of a voltage on a terminal of the first FET. In some embodiments, the second FET comprises a source follower. In some embodiments, the output conductor is a column bus. In some embodiments, the bias circuitry comprises at least one voltage source and at least one current sink. In some embodiments, the bias circuitry applies a voltage source to the first FET and applies a current sink to the second FET. In some embodiments, the bias circuitry concurrently applies a voltage source to the drain of the first FET and applies a current sink to the source of the second FET. In some embodiments, the output signal is dependent on the channel conductance of the second FET. In some embodiments, the first FET is operating under drain induced barrier lowering constraints and thereby is relatively insensitive to potential on its gate when the output signal is obtained from the second FET. In some embodiments, the first FET is operating under punch through mode constraints and thereby is relatively insensitive to potential on its gate when the output signal is obtained from the second FET. In some embodiments, the third FET is operated as a switch, biased in at least one of a triode region and a saturation region, and the first FET is biased at a high potential to induce drain induced barrier lowering in the first FET. In some embodiments, the output conductor is coupled to a terminal of the first FET, and the output conductor obtains a second output signal that has a magnitude from the first FET that is independent of variations of the gate voltage of the second FET. In some embodiments, the second FET is operating under at least one of drain induced barrier lowering and punch through mode constraints when the second output signal is obtained from the first FET. In some embodiments, the third FET is operated as a switch, biased in at least one of a triode region and a saturation region, and the second FET is biased at a high fixed potential to induce drain induced barrier lowering in the first FET. In some embodiments, the second FET is a chemically-sensitive field effect transistor (chemFET). In some embodiments, the chemFET is an ion sensitive field effect transistor (ISFET). In some embodiments, the output signal is based on a hydrolysis event. In some embodiments, the output signal relates to a nucleotide incorporation event detected by the second FET. In some embodiments, the output signal relates to detection of ions by the second FET.

In another exemplary embodiment, a chemical sensor is disclosed. The chemical sensor includes a first field effect transistor (FET) coupled to a first electrode, a second FET coupled to a second electrode, a switch coupled to the first FET and the second FET to concurrently couple the first FET and the second FET to readout circuitry in response to a select signal, and readout circuitry coupled to a terminal of the first FET via the switch to obtain a first signal from the first FET, and coupled to a terminal of the second FET via the switch to obtain a second signal from the second FET, wherein the signal from one FET is independent of the other FET. In some embodiments, the switch is serially connected to the first FET and the second FET. In some embodiments, the switch is disposed between the first FET and the second FET. In some embodiments, the first FET is in series with the second FET. In some embodiments, the first FET is operating under at least one of drain induced barrier lowering and punch through mode constraints when the signal is obtained from the second FET. In some embodiments, the second FET is operating under at least one of drain induced barrier lowering and punch through mode constraints when the signal is obtained from the first FET. In some embodiments, the first FET detects a first reaction at a first reaction site proximate to the first electrode and the second FET detects a second reaction at a second reaction site proximate to the second electrode. In some embodiments, a current source can be coupled to the first and second FET via the switch to provide a constant drain current to the first and second FET. In some embodiments, the readout circuitry includes an output conductor. In some embodiments, the output conductor is a column bus. In some embodiments, a first output node corresponding to the terminal of the first FET and a second output node corresponding to the terminal of the second FET are concurrently coupled to the column bus in response to the select signal. In some embodiments, a first reaction site is arranged proximate to the first electrode and a second reaction site is arranged proximate to the second electrode. In some embodiments, the first FET is coupled to the first electrode via a first floating gate. In some embodiments, the second FET is coupled to the second electrode via a second floating gate. In some embodiments, the first floating gate and the second floating gate each include a plurality of conductors electrically coupled to one another and separated by dielectric layers. In some embodiments, the first electrode is sensitive to ions. In some embodiments, the second electrode is sensitive to ions. In some embodiments, the second electrode is sensitive to ions different from ions the first electrode is sensitive to. In some embodiments, the first FET comprises a source follower. In some embodiments, the second FET comprises a source follower. In some embodiments, the first signal from the first FET is independent of a voltage on a terminal of the second FET. In some embodiments, the second signal from the second FET is independent of a voltage on a terminal of the first FET. In some embodiments, the first signal relates to a chemical reaction occurring within the first reaction site and proximate to the first electrode. In some embodiments, the second signal relates to a chemical reaction occurring within the second reaction site and proximate to the second electrode. In some embodiments, the first signal relates to detection of ions by the first FET. In some embodiments, the second signal relates to detection of ions by the second FET. In some embodiments, the first signal is based on a hydrolysis event. In some embodiments, the second signal is based on a second hydrolysis event. In some embodiments, the first signal relates to a nucleotide incorporation event detected by the first FET. In some embodiments, the second signal relates to a nucleotide incorporation event detected by the second FET.

In another exemplary embodiment, a transducer is disclosed. The transducer includes first and second chemical sensing surfaces for receiving respective first and second chemical input signals, first and second field-effect transistors (FETs) arranged in series and arranged to receive a common select signal, each FET respectively coupled to the first and second chemical sensing surfaces to provide respective first and second electrical output signals corresponding to the first and second chemical input signals, and a third FET shared by the first and second FETs to concurrently couple the first and second electrical output signals to respective first and second output nodes in response to the common select signal, wherein the first and second electrical output signals are read out asynchronously at the respective first and second output nodes. In some embodiments, the third FET couples the first electrical output signal to the first output node corresponding to a terminal of the first FET, and couples the second electrical output signal to the second output node corresponding to a terminal of the second FET. In some embodiments, a current source provides a bias current to the first and second FETs via the third FET. In some embodiments, the third FET couples a current source to the first and second FETs. In some embodiments, the third FET is a switch. In some embodiments, the first and second electronic output signals are provided at conduction terminals of the respective first and second FETs. In some embodiments, the first and second chemical sensing surfaces are respectively coupled to the first and second FETs via respective first and second floating gates. In some embodiments, the first and second FETs comprise source followers. In some embodiments, the first and second electrical output signals are based on a voltage at respective terminals of the first and second FETs. In some embodiments, first and second reaction sites are provided proximate to the first and second chemical sensing surfaces. In some embodiments, the first and second electrical output signals relate to chemical reactions occurring within the reaction sites and proximate to the first and second chemical sensing surfaces. In some embodiments, the first and second electrical output signals relate to detection of ions. In some embodiments, the first and second chemical sensing surfaces are sensitive to ions. In some embodiments, the first and second electrical output signals are based on a hydrolysis event occurring proximate to at least one of the first and second chemical sensing surfaces. In some embodiments, the first and second electrical output signals relate to a nucleotide incorporation event. In some embodiments, the first and second chemical input signals relate to a nucleotide incorporation event.

In another exemplary embodiment, a semiconductor device for detecting a change in ion concentration of a sample is disclosed. The device includes a chemically sensitive field effect transistor (chemFET) having a first terminal and a second terminal, a field effect transistor (FET) having a source terminal and a drain terminal, the FET in series with the chemFET, a select FET having a first terminal coupled to the second terminal of the chemFET and having a second terminal coupled to the source terminal of the FET, the select circuit couples the FET to a readout circuit via the chemFET, and a readout circuit for obtaining an output signal at the first terminal of the chemFET that is independent of a voltage on the source terminal of the FET. In some embodiments, the chemFET comprises a source follower. In some embodiments, the select circuit comprises a switch. In some embodiments, the FET is operating under at least one of drain induced barrier lowering and punch through mode constraints when the output signal is obtained from the chemFET. In some embodiments, the select FET couples the FET and the chemFET to a bias current from a current source, couples the FET and the chemFET to the readout circuit. In some embodiments, the select FET further couples the FET and the chemFET to the readout circuit. In some embodiments, the chemFET comprises an ion sensing layer coupled to a field-effect transistor (FET) via a floating gate. In some embodiments, the ion sensing layer is exposed to the sample to produce the output signal representing a chemical reaction occurring proximate to the ion sensing layer. In some embodiments, the FET is coupled to a reaction site via the ion sensing layer.

In another exemplary embodiment, a system for reading out serially-connected chemFETs is disclosed. The system includes at least two serially-connected chemically-sensitive field-effect transistors (chemFETs), each field-effect transistor (FET) of the chemFETs coupled to a sensing electrode via a floating gate, readout circuitry for independently reading out each of the at least two serially-connected chemFETs at a terminal of the chemFET to be read out, and a select transistor in series with the at least two serially-connected chemFETs wherein the select transistor concurrently couples the at least two serially-connected chemFETs to the readout circuitry. In some embodiments, the readout of one chemFET is isolated from a voltage on a terminal of the other chemFET. In some embodiments, the at least two serially connected chemFETs share a common row line. In some embodiments, the select transistor is disposed between two of the at least two serially connected chemFETs.

In another exemplary embodiment, an array of chemical sensors is disclosed. The array of chemical sensors, a current source coupled to a row line of the array, a row select field effect transistor (FET) disposed in series between a pair of serially connected chemically-sensitive field effect transistors (chemFETs), the row select FET to sample a voltage level on the row line at an output node, the voltage level associated with only one chemFET of the pair of chemFETs, and an output node on the row line and coupled to [col. level] circuitry to alternately readout the sampled voltage level from one of the chemFETs of the pair and then the other, wherein the voltage lever obtained from one chemFET is read out in isolation from the other chemFET.

In another exemplary embodiment, a sensor device is disclosed. The sensor includes a first transistor having first and second conduction terminals (i.e. source/drain terminals) and a gate, the gate including a first sensor surface adapted for exposure to an electrolyte cell, a second transistor having first and second conduction terminals and a gate, the gate including a second sensor surface adapted for exposure to an electrolyte cell, a first column line connected to the first conduction terminal of the first transistor, a second column line connected to the second conduction terminal of the second transistor, and a select transistor between the second conduction terminal of the first transistor and the first conduction terminal of the second transistor, the select transistor having a gate. In some embodiments, a row decoder is connected to the gate of the select transistor, and a column biasing circuitry connected to the first and second column lines and having an output, the column biasing circuits having a first mode in which a drain voltage is applied to the first column line and the output is coupled to the second column line, and a second mode in which a drain voltage is applied to the second column line and the output is coupled to the first column line. In some embodiments, in the first mode, a voltage or current on the output of the column biasing circuitry indicates a voltage on the gate of the second transistor; and in the second mode, a voltage or current on the output of the column biasing circuitry indicates voltage on the gate of the first transistor. In some embodiments, sensing circuitry is connected to the output of the column biasing circuitry, and wherein during the first mode, a voltage within a specified operating range (i.e. the operating range of voltages within which the device is designed to operate) induced by charge on the gate of the first transistor contributes, if at all, to inducing a voltage or current on the output by an amount that is below a noise limit/below a quantization error of the sensing circuitry, and during the second mode, a voltage within the specified operating range induced by charge on the gate of the second transistor contributes, if at all, to inducing a voltage or current on the output by an amount that is below the noise limit. In some embodiments, the sensing circuitry includes an analog to digital converter, and produces a digital sample signal having a least significant bit which corresponds to a quantization value of voltage or current on the output, and wherein the noise limit is equal to less than said quantization value. In some embodiments, the column biasing circuitry includes a current source, and wherein during the first mode, the second column line is connected to the current source, and during the second mode, the first column line is connected to the current source. In some embodiments, an electrolyte cell or cells is/are coupled to first and second sensor surfaces.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

Semiconductor devices and/or sensors for detecting a chemical and/or biological reaction are described herein. The sensors can be arranged to provide a sensor array. Sensors of the array can be arranged in rows and columns. Alternatively, sensors can be arranged in a random (unordered) fashion on any medium suitable to support sensors that can detect a chemical and/or biological reaction. A sensor can have a sensitive area that is suitable for detecting a chemical and/or biological reaction. For example, the sensitive area can comprise a surface adapted for exposure to an analyte, where the surface is a material that can be selected based on its sensitivity to particular ions in the analyte, as is more fully disclosed below with reference to FIG. 3. The semiconductor devices and/or sensors can detect a chemical and/or biological reaction occurring within or proximate to operationally associated reaction regions. The reaction regions can be wells, dimples, rows, discrete sites, reaction sites, cavities, microwells, or any other suitable structural feature for containing or retaining a reaction. In some embodiments, the reaction region has a bottom and a sidewall. In some embodiments, the surface adapted for exposure to an analyte can comprise an electrode. A variety of electrically conductive materials can be used for the electrode, such as metals or ceramics. In some embodiments, the electrode can extend vertically up a sidewall of the reaction region. The electrode may cover any suitable area or location of the reaction region. In some embodiments, the sidewalls can be at some predetermined angle. The sidewalls may be at an angle from 0 degrees to 180 degrees. The distance that the substantially vertical portion extends along the sidewall can be defined by the thickness of a dielectric material that forms the opening of the reaction region. The dielectric material can be deposited or grown using any suitable process for forming a sensor or combination thereof (e.g. thin film deposition, vapor deposition, oxidation, etc.).

Figure 1:
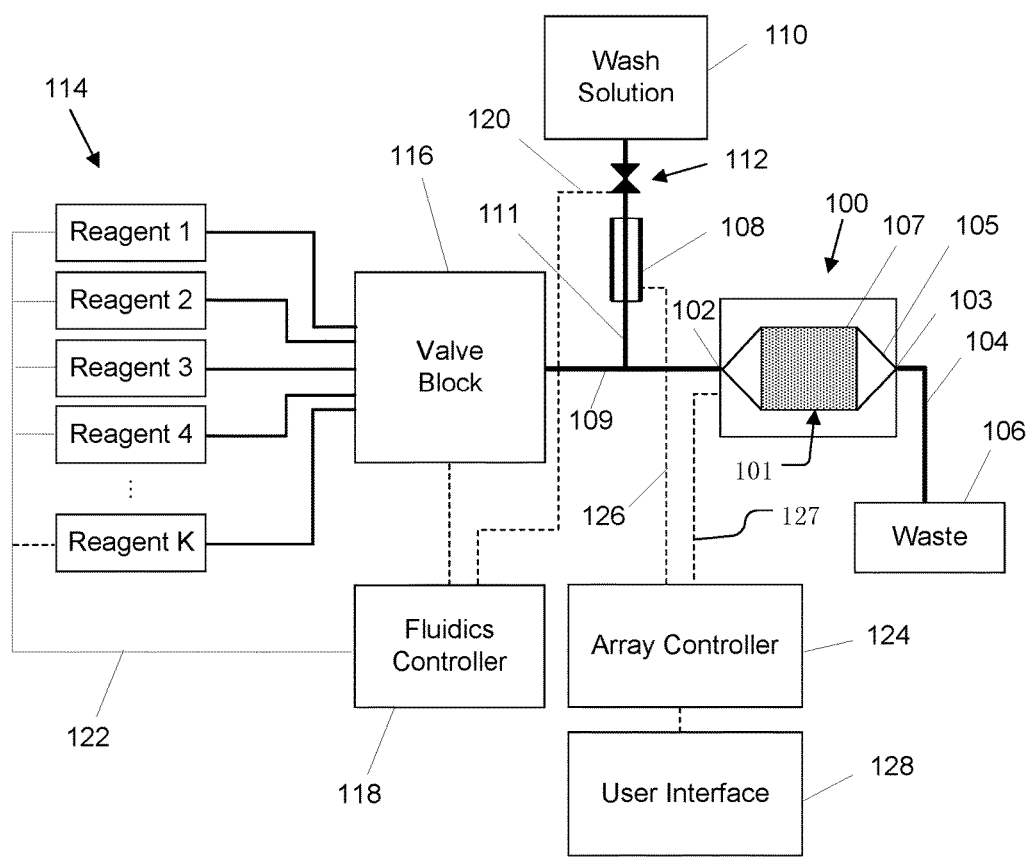
FIG. 1 illustrates a block diagram of components of a system for nucleic acid sequencing according to an exemplary embodiment.

FIG. 1 illustrates a block diagram of components of a system for nucleic acid sequencing according to an exemplary embodiment. In some embodiments, the components include flow cell 101 on integrated circuit device 100, reference electrode 108, plurality of reagents 114 for sequencing, valve block 116, wash solution 110, valve 112, fluidics controller 118, lines 120/122/126, passages 104/109/111, waste container 106, array controller 124, and user interface 128. Integrated circuit device 100 includes microwell array 107 overlying a sensor array that includes devices as described herein. Flow cell 101 includes inlet 102, outlet 103, and flow chamber 105 defining a flow path of reagents over microwell array 107. Reference electrode 108 can be of any suitable type or shape, including a concentric cylinder with a fluid passage or a wire inserted into a lumen of passage 111. Reagents 114 can be driven through the fluid pathways, valves, and flow cell 101 by pumps, gas pressure, or other suitable methods, and can be discarded into waste container 106 after exiting outlet 103 of flow cell 101. Fluidics controller 118 can control driving forces for reagents 114 and operation of valve 112 and valve block 116 with suitable software. Microwell array 107 includes an array of reaction regions which are operationally associated with corresponding sensors in the sensor array. For example, each reaction region can be coupled to a sensor suitable for detecting an analyte or reaction property of interest within that reaction region. Microwell array 107 can be integrated in integrated circuit device 100, so that microwell array 107 and the sensor array are part of a single device or chip. Flow cell 101 can have a variety of configurations for controlling the path and flow rate of reagents 114 over microwell array 107. Array controller 124 provides bias voltages and timing and control signals to integrated circuit device 100 for reading the sensors of the sensor array. Array controller 124 also provides a reference bias voltage the reference electrode 108 to bias reagents 114 flowing over microwell array 107.

Array controller 124 collects and processes output signals from the sensors of the sensor array through output ports on integrated circuit device 100 via bus 127. Array controller 124 can be a computer or other computing means. Array controller 124 can include memory for storage of data and software applications, a processor for accessing data and executing applications, and components that facilitate communication with the various components of the system in FIG. 1. The values of the output signals of the sensors can indicate physical and/or chemical parameters of one or more reactions taking place in the corresponding reaction regions in microwell array 107. For example, in some exemplary embodiments, the values of the output signals can be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No 61/428,097, filed Dec. 29, 2010, which are all incorporated by reference herein in their entirety. User interface 128 can display information about flow cell 101 and the output signals received from sensors in the sensor array on integrated circuit device 100. User interface 128 can also display instrument settings and controls, and allow a user to enter or set instrument settings and controls.

In some embodiments, fluidics controller 118 can control delivery of individual reagents 114 to flow cell 101 and integrated circuit device 100 in a predetermined sequence, for predetermined durations, and/or at predetermined flow rates. Array controller 124 can collect and analyze the output signals of the sensors related to chemical and/or biological reactions occurring in response to the delivery of reagents 114. The system can also monitor and control the temperature of integrated circuit device 100 so that reactions take place and measurements are made at a known predetermined temperature. The system can be configured to let a single fluid or reagent contact reference electrode 108 throughout an entire multi-step reaction during operation. Valve 112 can be shut to prevent any wash solution 110 from flowing into passage 109 as reagents 114 are flowing. Although the flow of wash solution can be stopped, there can still be uninterrupted fluid and electrical communication between reference electrode 108, passage 109, and microwell array 107. The distance between reference electrode 108 and the junction between passages 109 and 111 may be selected so that little or no amount of the reagents flowing in passage 109, which may diffuse into passage 111, will reach reference electrode 108. In some embodiments, wash solution 110 can be selected as being in continuous contact with reference electrode 108, which can be especially useful for multi-step reactions using frequent wash steps.

Figure 2:
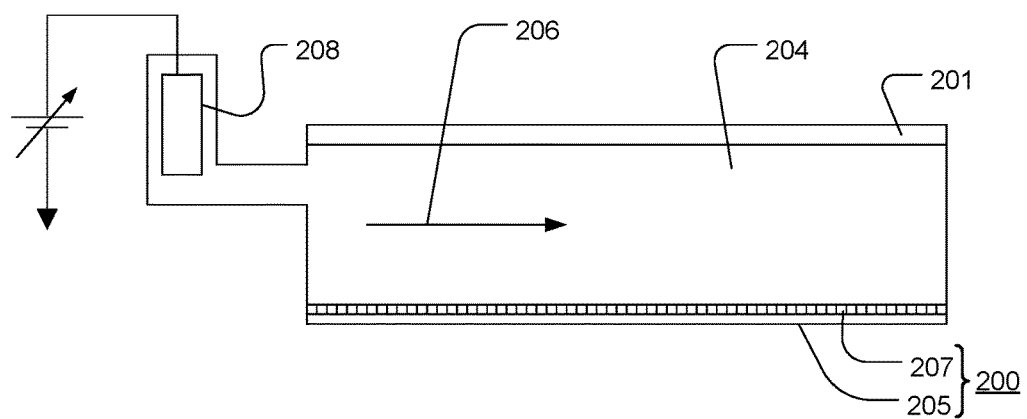
FIG. 2 illustrates a cross-sectional view of a portion of the integrated circuit device and flow cell according to an exemplary embodiment.

FIG. 2 illustrates a cross-sectional view of a portion of the integrated circuit device and flow cell according to an exemplary embodiment. FIG. 2 includes integrated circuit device 200, flow cell 201 and reference electrode 208. During operation, flow chamber 204 of flow cell 201 can confine reagent flow 206 of delivered reagents across open ends of the reaction regions in microwell array 207. The volume, shape, aspect ratio (such as base width-to-well depth ratio), and other dimensional characteristics of the reaction regions can be selected based on the nature of the reaction taking place, as well as the reagents, products/byproducts, or labeling techniques (if any) that are employed. The sensors of sensor array 205 can be responsive to (and generate output signals related to) chemical and/or biological reactions within associated reaction regions in microwell array 207 to detect an analyte or reaction property of interest. In some embodiments, the detection is the detection of fluorescence. The sensors of sensor array 205 can be chemically sensitive field-effect transistors (chemFETs), such as ion-sensitive field effect transistors (ISFETs). Examples of sensors and array configurations that can be used in embodiments are described in U.S. Patent Application Publication No. 2010/0300559, filed May 24, 2010, No. 2010/0197507, filed Oct. 5, 2012, No. 2010/0301398, filed Oct. 5, 2012, No. 2010/0300895, May 4, 2010, No. 2010/0137143, filed May 29, 2009, and No.

2009/0026082, filed Dec. 17, 2007, and U.S. Pat. No. 7,575,865,filed Aug. 1 2005, each of which are incorporated by reference herein in their entirety. In some embodiments, other sensor can be used, including but not limited to thermistors and optical sensors, for example.

Figure 3:
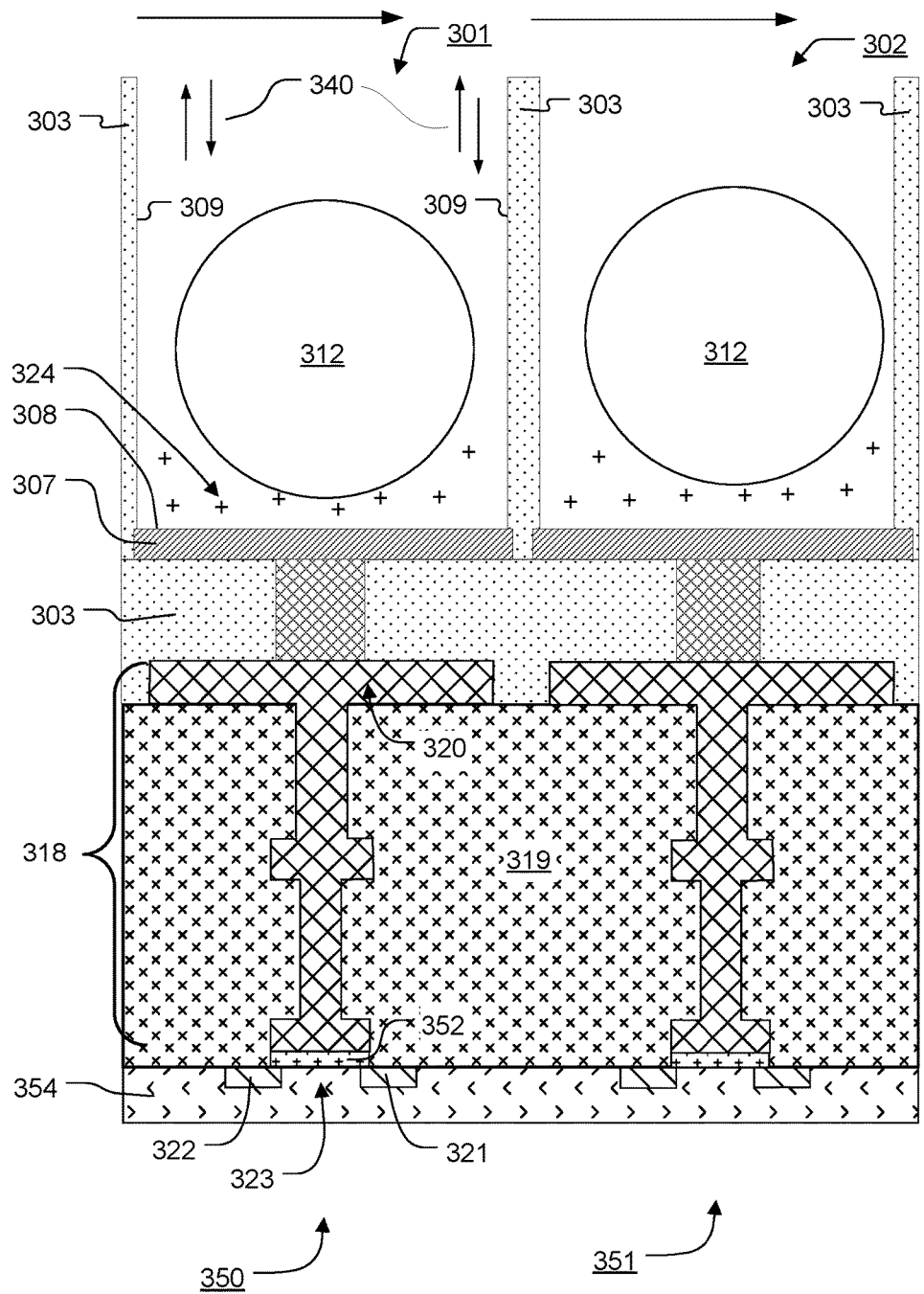
FIG. 3 illustrates cross-sectional view of representative sensors/detectors and corresponding reaction regions according to an exemplary embodiment.

FIG. 3 illustrates cross-sectional view of representative sensors/detectors and corresponding reaction regions according to an exemplary embodiment. In some embodiments the sensors can be chemical sensors. FIG. 3 shows two exemplary sensors 350, 351, representing a small portion of a sensor array that can include millions of sensors; even billions of sensors are contemplated. For example, the sensor array can comprise between 100 and 1,000 sensors, between 100 and 10,000 sensors, between 10,000 and 100,000 sensors, between 100,000 and 1,000,000 sensors, between 1,000,000 and 40,000,000 sensors, between 10,000,000 and 165,000,000 sensors, between 100,000,000 and 660,000,000 sensors, between 1,000,000,000 and 5,000,000,000 sensors, between 5,000,000,000 and 9,000,000,000 sensors, and up to 10,000,000,000 sensors. Windowing of the array is contemplated such that data can be obtained from all or fewer than all of the sensors. Sensor 350 is coupled to corresponding reaction region 301, and sensor 351 is coupled to corresponding reaction region 302. The two illustrated reaction regions are chemically and electrically isolated from one another and from neighboring reaction regions. The dielectric material 303 defines the reaction regions 301/302 which can be within an opening defined by an absence of dielectric material. Dielectric material 303 can comprise one or more layers of material, such as silicon dioxide or silicon nitride or any other suitable material or mixture of materials. The dimensions of the openings, and their pitch, can vary from embodiment to embodiment. In some embodiments, the openings can have a characteristic diameter, defined as the square root of 4 times the plan view cross-sectional area (A) divided by Pi (e.g., sqrt($4*A/\pi$), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or not greater than 0.1 micrometers. The plan view area of the sensor is determined in part by the width (or diameter) of reaction regions and can be made small to provide a high density array. The footprint of a sensor can be determined and/or reduced by modifying the width (e.g. diameter) of the reaction region. In some embodiments, the density of the array can be increased or decreased based on the diameter selected for the reaction region. Low noise sensors can be provided in a high density array by reducing device and interconnect overhead, including gate area and contact area. Additional examples of sensors and their corresponding reaction regions according to additional exemplary embodiments are described in Fife et al., U.S. patent application Ser. No. 14/198,382, filed Mar. 5, 2014, based on U.S. Prov. Pat. Appl. Nos. 61/868,739, filed Aug. 22, 2013, and 61/790,866, filed Mar. 15, 2013; Fife et al., U.S. patent application Ser. No. 14/197,710, filed Mar. 5, 2014, based on U.S. Prov. Pat. Appl. Nos. 61/868,736, filed Aug. 22, 2013, and 61/790,866, filed Mar. 15, 2013; Fife et al., U.S. patent application Ser. No. 14/198,402, filed Mar. 5, 2014, based on U.S. Prov. Pat. Appl. Nos. 61/868,942, filed Aug. 22, 2013, and 61/790,866, filed Mar. 15, 2013; Fife et al., U.S. patent application Ser. No. 14/197,741, filed Mar. 5, 2014, based on U.S. Prov. Pat. Appl. Nos. 61/868,947, filed Aug. 22, 2013, and 61/790,866, filed Mar. 15, 2013; and Fife et al., U.S. patent application Ser. No. 14/198,417, filed Mar. 5, 2014, based on U.S. Prov. Pat. Appl. Nos. 61/900,907, filed Aug. 22, 2013, and 61/790,866, filed Mar. 15, 2013, which are all incorporated by reference herein in their entirety.

Sensor 350 is representative of the sensors in the sensor array. In the illustrated example, sensor 350 is a chemically-sensitive field effect transistor (chemFET), more specifically an ion-sensitive field effect transistor (ISFET) in this example. Sensor 350 includes floating gate structure 318 having sensor plate 320 coupled to reaction region 301 by electrode 307 which can have a surface adapted for contact with an analyte. Sensor plate 320 is the uppermost floating gate conductor in floating gate structure 318. In the illustrated example, floating gate structure 318 includes multiple patterned layers of conductive material within layers of dielectric material 319. Sensor 350 also includes conduction terminals including source/drain region 321 and source/drain region 322 within semiconductor substrate 354. Source/drain region 321 and source/drain region 322 comprise doped semiconductor material having a conductivity type different from the conductivity type of substrate 354. For example, source/drain region 321 and source/drain region 322 can comprise doped P-type semiconductor material, and the substrate can comprise doped N-type semiconductor material. Channel region 323 separates source/drain region 321 and source/drain region 322. Floating gate structure 318 overlies channel region 323, and is separated from substrate 354 by gate dielectric 352. Gate dielectric can be silicon dioxide, for example. Alternatively, other suitable dielectrics can be used for gate dielectric 352 such as, for example materials with higher dielectric constants, silicon carbide (SiC), silicon nitride ($Si_3N_4$), Oxynitride, aluminum nitride (AlN), hafnium dioxide ($HfO_2$), tin oxide ($SnO_2$), cesium oxide (CeO2), titanium oxide (TiO2), tungsten oxide (WO3), aluminum oxide (Al2O3),lanthanum oxide (La2O3), gadolinium oxide and others, and any combination thereof.

In some embodiments, sensor 350 includes electrode 307 overlying and in communication with an uppermost floating gate conductor in the plurality of floating gate conductors. Upper surface 308 of electrode 307 defines a bottom surface of a reaction region for the sensor. Upper surface 308 of electrode 307 can act as the sensor surface of the sensitive area for sensor 350. Electrode 307 can comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, hydroxide, phosphate, and nitrate can also be used. In the illustrated example, electrode 307 is shown as a single layer of material. More generally, the electrically electrode can comprise one or more layers of a variety of electrically conductive materials, such as metals or ceramics, or any other suitable conductive material or mixture of materials, depending upon the implementation. The conductive material can be any suitable metallic material or alloy thereof, or can be any suitable ceramic material, or a combination thereof. Examples of metallic materials include aluminum, copper, nickel, titanium, silver, gold, platinum, hafnium, lanthanum, tantalum, tungsten, iridium, zirconium, palladium, or any suitable material or combination thereof. Examples of ceramic materials include one of titanium nitride, titanium aluminum nitride, titanium oxynitride, tantalum nitride, or any suitable combination thereof. In some embodiments, an additional sensing material (not shown) is deposited on upper surface 308 of electrode 307. In some embodiments, the electrode can be titanium nitride, and titanium oxide or titanium oxynitride can be grown on the upper surface 308 during manufacturing and/or during exposure to fluids during use. Whether an oxide is formed on the upper surface depends on the conductive material used, the manufacturing processes performed, and/or the conditions under which the sensor is operated. The electrode can be formed in various shapes (width, height, etc.) depending on the materials and/or etch techniques and/or fabrication processes etc. used during the manufacture process.

In some embodiments, reactants, wash solutions, and other reagents can move in and out of reaction region 301 by diffusion mechanism. Sensor 350 is responsive to (and can generate an output signal related to) charge 324 proximate to electrode 307. For example, when the sensor is coupled to an analyte, the sensor can be responsive to an electrolytic potential at the sensor surface. The responsiveness of the sensor can relate to the amount of charge that is present proximate to the electrode 307. The presence of charge 324 in an analyte solution can alter the surface potential at the interface between the analyte solution and upper surface 308 of electrode 307. For example, the surface potential can be altered by protonation or deprotonation of surface groups caused by the ions present in the analyte solution. In another example, the charge of surface functionality or absorbed chemical species can be altered by analytes in solution. Changes in the amount of charge present can cause changes in the voltage on floating gate structure 318, which in turn can cause an effective change in the threshold voltage of the transistor of sensor 350. The potential at the interface can be measured by measuring the current in channel region 323 between source region 321 and drain region 322. As a result, sensor 350 can be used directly to provide a current-based output signal on an array line connected to source region 321 or drain region 322, or indirectly with additional circuitry to provide a voltage-based output signal. Charge can be more highly concentrated near the bottom of reaction region 301. Accordingly, in some embodiments variations in the dimensions of the electrode can have an effect on the amplitude of the signal detected in response to charge 324.

In some embodiments, reactions carried out in reaction region 301 may be analytical reactions to identify or determine characteristics or properties of an analyte of interest. Such reactions can generate directly or indirectly products/byproducts that affect the amount of charge adjacent to electrode 307. If such products/byproducts are produced in small amounts or rapidly decay or react with other constituents, multiple copies of the same analyte may be analyzed in reaction region 301 at the same time in order to increase the output signal generated. In some embodiments, multiple copies of an analyte may be attached to solid phase support 312, either before or after being deposited into reaction region 301. Solid phase support 312 may be a particle, a microparticle, a nanoparticle. In some embodiments, the analyte may be attached to a bead which may be solid or porous and can further comprise a gel, or the like, or any other suitable solid support that may be introduced to a reaction region. In some embodiments, copies of an analyte may be located in a solution proximal to a sensor of a reaction region. Alternatively, copies of an analyte can bind directly to the surface of the sensor to capture agents includes the material on the surface or if there are pores on the surface (for example, copies of an analyte can bind directly to electrode 307). The solid phase support may be of varied size, for example, in a range of 100 nm to 10 micrometers. Further, the solid support may be positioned in the opening at various places. For a nucleic acid analyte, multiple, connected copies may be made by rolling circle amplification (RCA), exponential RCA, polymerase chain reaction (PCR) or like techniques, to produce an amplicon without the need of a solid support.

In various exemplary embodiments, the methods, and systems described herein can advantageously be used to process and/or analyze data and signals obtained from a biological reaction, including amplification or electronic or charged-based nucleic acid sequencing. In electronic or charged-based sequencing (such as pH-based sequencing), a nucleotide incorporation event can be determined by detecting ions (e.g., hydrogen ions) that are generated as natural products of polymerase-catalyzed nucleotide extension reactions. This can be used to sequence a sample or template nucleic acid, which can be a fragment of a nucleic acid sequence of interest, for example, and which can be directly or indirectly attached as a clonal population to a solid support, such as a particle, microparticle, bead, etc. The sample or template nucleic acid can be operably associated to a primer and polymerase and can be subjected to repeated cycles or "flows" of deoxynucleoside triphosphate ("dNTP") addition (which can be referred to herein as "nucleotide flows" from which nucleotide incorporations can result) and washing. The primer can be annealed to the sample or template so that the primer's 3' end can be extended by a polymerase whenever dNTPs complementary to the next base in the template are added. Based on the known sequence of nucleotide flows and on measured output signals of the sensors indicative of ion concentration during each nucleotide flow, the identity of the type, sequence and number of nucleotide(s) associated with a sample nucleic acid present in a reaction region coupled to a sensor can be determined.

A sensor array for use in an analog domain can comprise numerous five terminal devices arranged in rows and columns, for example. The five terminal device can comprise three inputs and two outputs, wherein one of the three inputs is a select signal and the other two inputs can be analog signals. The five terminal devices are operated for reading out the analog signals using source follower configurations.

Figure 4:
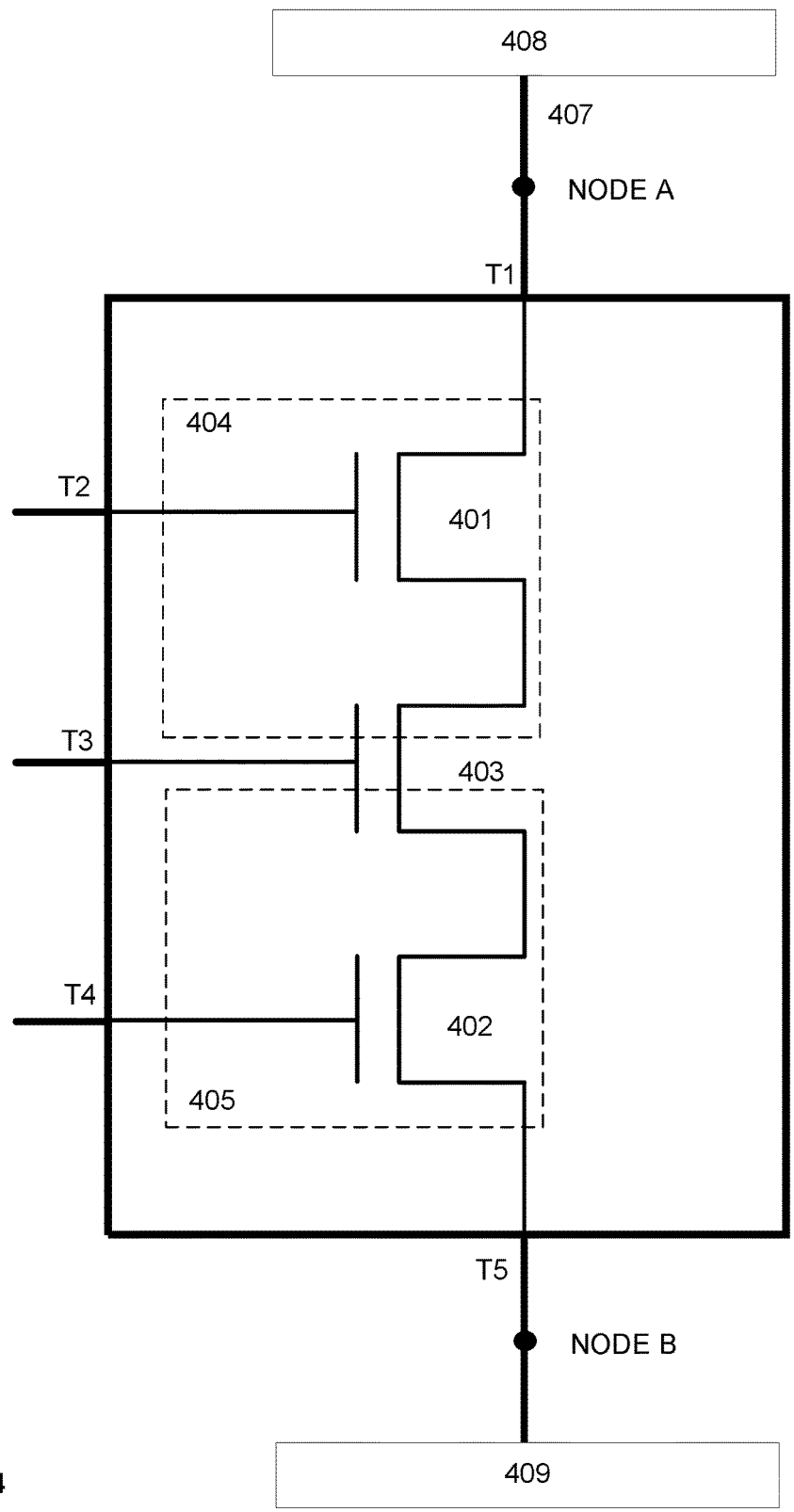
FIG. 4 illustrates a five terminal device according to an exemplary embodiment.

FIG. 4 illustrates a five terminal device according to an exemplary embodiment. In some embodiments, at least one of or all of device(s) 401, 402, and/or 403 can be a transistor. In some embodiments, at least one of or all of device(s) 401, 402, and/or 403 can be a field-effect transistor (FET). The three exemplary devices are shown as being connected in series such that device 401 is connected in series to device 403 and device 403 is connected in series to device 402. In some embodiments, device 403 can be a select transistor. In some embodiments, device 403 can be a switch. Device 403 can be between device 401 and 402 but need not be. Any serial arrangement of the three devices is possible, including but not limited to device 401 connected in series to device 402 and device 402 connected in series to device 403; device 403 connected in series to device 401 and device 401 connected in series to device 402; device 403 connected in series to device 402 and device 402 connected in series to device 401, for example. Devices 401, 402, and 403 can be disposed along column line 407, for example. As shown in FIG. 4, device 403 can be shared by device 401 and device 402. Device 401 and device 403 can collectively be referred to as pixel 404. Device 402 and device 403 can collectively be referred to as pixel 405. Pixel 404 and 405 can together be referred to as a pixel doublet.

The five terminal device illustrated in FIG. 4 can operate as follows: a select signal can be applied to terminal 3 (T3) to select devices 401 and 402 (by means of a select transistor, device 403, for example). With both devices 401 and 402 selected, device 402 can be biased at a high fixed potential to turn on the channel as a result of drain induced barrier lowering and/or punch through in device 402 so that the current is largely unaffected by the electrolytic potential on the electrode, and device 401 can be read out at terminal 1 (T1) (or on a line/by a device connected to NODE A, for example), whereby the signal (at T2) that is read out is independent of a signal at T4. Terminal 1 is coupled to bias circuitry 408. Bias circuitry 408 includes at least one current sink/source and at least one voltage source. Put another way, the signal at T2 can be obtained via device 401 without an attenuation of the signal at T4 by operating device 402 in punch through mode (PTM) or in drain induced barrier lowering (DIBL) while device 401 is biased in at least one of a triode region and a saturation region. The effects of PTM and/or DIBL can be advantageously used to effectively 'knock out' or mask other devices which are serially connected to a device of interest when the devices are concurrently selected. While FIG. 4 illustrates a select transistor shared by two devices 401 and 402, a plurality of devices which are serially connected and share a common select transistor is contemplated. For example, depending on the technology node and material(s)/fabrication process(es) used, connecting up to 10,000,000,000 devices is contemplated. According to some embodiments, device 401 can be configured as a source follower. According to some embodiments, device 402 can be configured as a source follower. According to some embodiments, the output signal obtained when reading out device 401 is dependent on the threshold voltage of device 401. The output signal can be read out on an output conductor, such as a column bus, for example. Thus, device 403 can be seen as concurrently coupling device 401 and 402 to the output conductor in response to a select signal. Put another way, the device 403 couples device 401 and device 402 in current flow communication with an output conductor.

The readout operation can be 'flipped' and the signal at T4 can be read via device 402 out without signal corruption from device 401(at T2). For example, a select signal can be applied to terminal 3 (T3) to select devices 401 and 402 (by means of a select transistor, device 403, for example). With both devices 401 and 402 selected, device 401 can be biased at a high fixed potential to induce drain induced barrier lowering in device 401, and device 402 can be read out at terminal 1 (T5) (or on a line/by a device connected to NODE B, for example), whereby the signal (at T4) that is read out is independent of a signal at T2. Terminal 2 is coupled to bias circuitry 409. Bias circuitry 409 includes at least one current sink/source and at least one voltage source. Bias circuitry 408 can be the same circuitry as bias circuitry 409 or it can be different. Put another way, the signal at T4 can be obtained via device 402 without an attenuation of the signal at T2 by operating device 401 in punch through mode (PTM) or in drain induced barrier lowering (DIBL) while device 402 is biased in at least one of a triode region and a saturation region.

A sensor array can comprise a plurality of electronic detection sensors (chemical/biological sensors, for example). Each sensor can comprise a chemically-sensitive field effect transistor (chemFET) configured to provide at least one output signal relating to a concentration of ions proximate to a sensor of the array. Additionally, in some embodiments, the array can further comprise at least one row select shift register to enable respective rows of the plurality of rows, and at least one column select shift register to acquire sensor (e.g. chemFET) output signals from respective columns of the plurality of columns. Multiple columns can form an array of sensors/detectors (or, sensor/detector doublets) arranged in rows and columns. A sensor array can comprise a plurality of sensors formed in columns with each column including a plurality of rows of sensors. When a row selection line is activated, a row selection device (e.g. a FET) forms a channel due to the gate voltage exceeding a threshold voltage and acts like a switch. When the row selection is deactivated, the channel is diminished. Alternatively, in a high density array, a row selection device may not be able to be completely turned "on" or "off." Rather, it can approximate a switch. When the gate terminal is substantially lower than the source terminal of the row selection transistor, isolation of the signal can be achieved and the sensor with the active row selection can be read effectively without input from deactivated sensors. For an array with many rows, it can be preferable to achieve a given level of isolation for each row selection device. That is, the requirements for the row selection device can depend on the number of rows the array.

Figure 5:
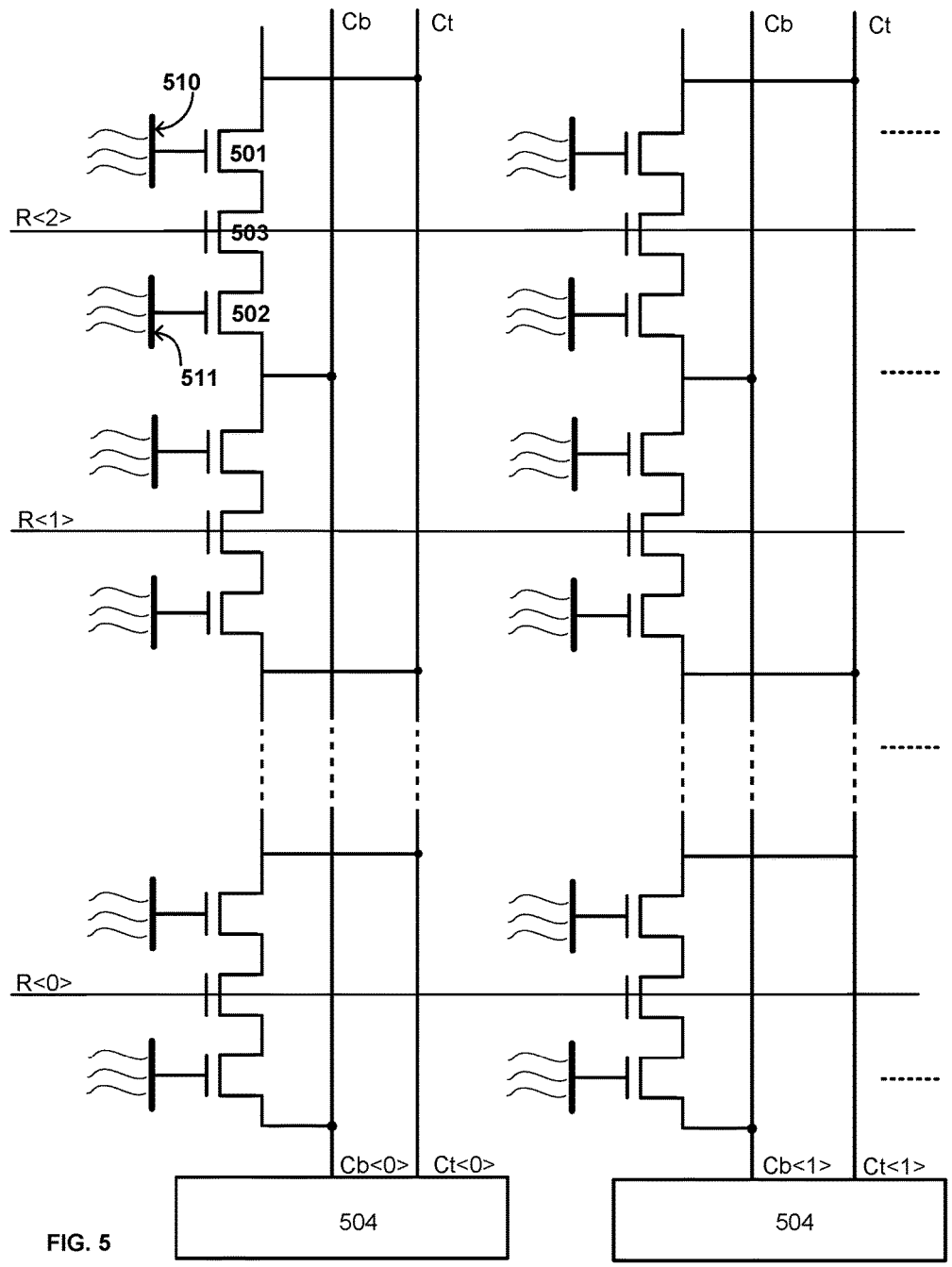
FIG. 5 illustrates a sensor array according to an exemplary embodiment.

FIG. 5 illustrates a sensor array according to an exemplary embodiment. As shown, device 501 is coupled to electrode 510 and device 502 is coupled to electrode 511. Device 503 is shared by device 501 and device 502. Device 503 is shown as being connected between device 501 and device 502; however, this need not be, as explained above regarding device layout/connectivity. In some embodiments, device 501 can be directly coupled to electrode 510, and device 502 can be directly coupled to electrode 511. Alternatively, device 501 can be coupled to electrode 510 via a floating gate as described herein with respect to FIG. 3. Further, device 502 can be optionally coupled to electrode 511 via a floating gate as described herein with respect to FIG. 3, for example. Additionally, a reaction region such as those described herein can be operationally coupled to the electrodes 510 and 511 either directly or indirectly. Referring to device 501, a first source/drain terminal of device 501 is coupled to a column line Ct (output conductor, top), and a second terminal of device 501 is coupled to a source/drain terminal of device 503. The first and second terminals of device 501 can be directly or indirectly coupled to Ct and device 503, respectively. The other terminal of device 503 is connected to a source/drain terminal of device 502. The other source/drain terminal of device 502 is coupled to column line Cb (output conductor, bottom). The first and second terminals of device 502 can be directly or indirectly coupled to Cb and device 503, respectively. Electrodes 510, 511 can comprise any of the afore-mentioned materials associated with the sensitive area and any other material which is suitable for receiving an input signal, for example, a chemical input signal. A reaction region such as those described herein can be operationally coupled to the electrode 511. Output signals from devices 501 and 502 can be individually, independently read out on respective column lines Ct and Cb. Column lines Cb and Ct are shown as connected to output/readout circuitry 504 which is described in further detail below (e.g. 604 in FIG. 6). The gate of device 503 is coupled to a row line R<2> for providing a select signal to select device 503. Devices 501, 502, and 503 are shown as NMOS transistors, but other types of transistors can be used, such as PMOS, for example.

Two serially connected sensors (i.e. a transistor coupled to an electrode, for example) concurrently selected by a common switch can be asynchronously read out to obtain independent output signals on respective output conductors connected to output/readout circuitry. The bias circuitry can comprise a combination of current sources and sinks for providing appropriate bias voltages to the sensors responsive to various timing and control signals provided by array controller 124. The two output conductors can be provided to a multiplexer such that a series of discrete output signals can be obtained.

Figure 6:
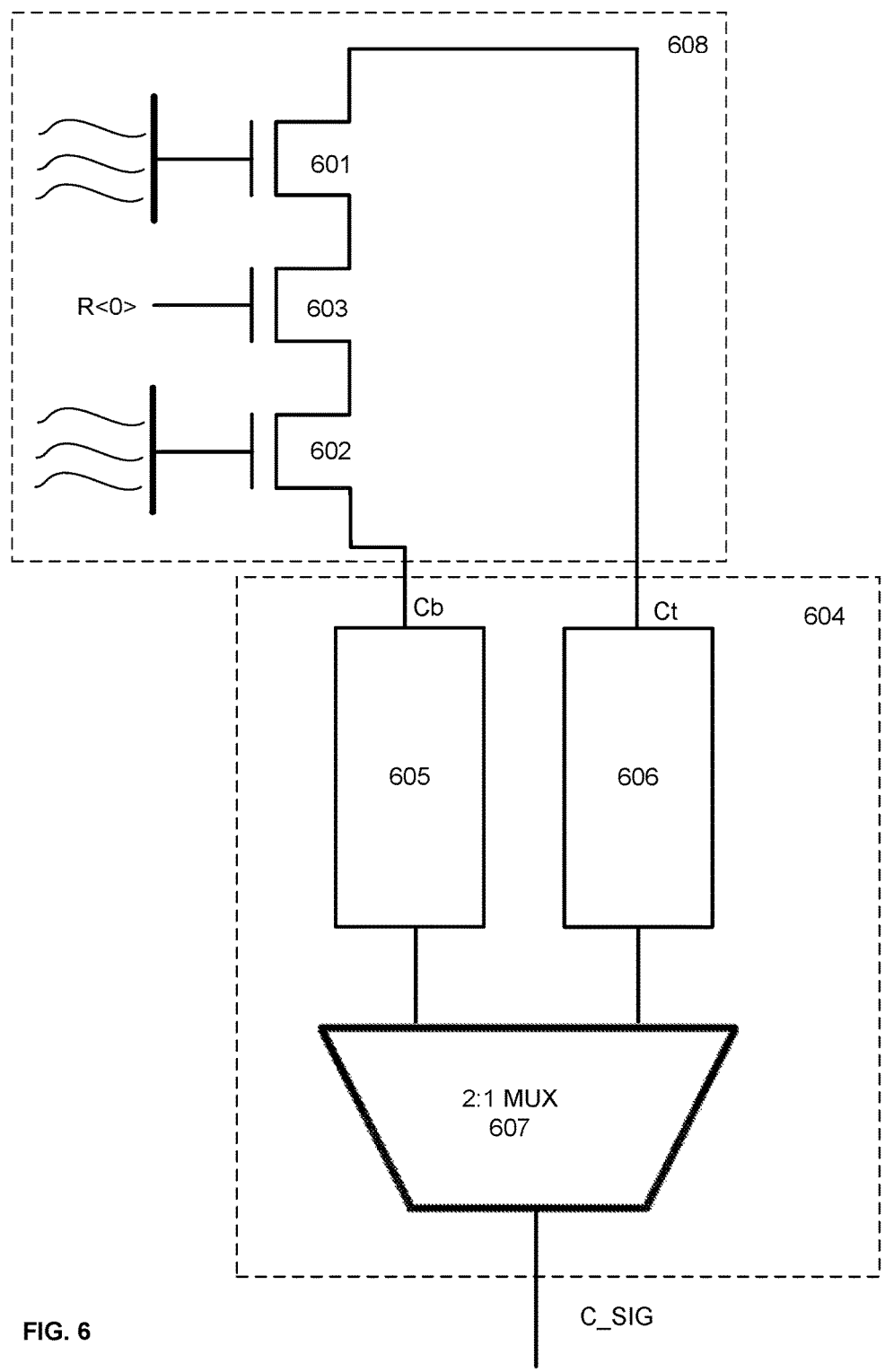
FIG. 6 illustrates a sensor doublet and readout circuitry according to an exemplary embodiment.

FIG. 6 illustrates an exemplary sensor doublet 608 and readout circuitry 604 according to an exemplary embodiment. In some embodiments, devices 601, 602, and 603 can be operated in a similar fashion as described herein with respect to FIG. 4. For example, a signal (e.g., an analog signal) present at the gate of device 601 can be read out without signal corruption from a signal (e.g., another analog signal) present at the gate of device 602. For example, a select signal (e.g., a row select signal R at R<0>) can be applied to the gate terminal of device 603 to select devices 601 and 602. With both devices 601 and 602 selected, device 602 can be biased at a high fixed potential to induce drain induced barrier lowering in device 602, and device 601 can be read out on Ct, whereby the signal that is read out is independent of a signal on the gate terminal of device 602. Put another way, the signal on the gate of device 601 can be obtained without an attenuation of the signal on the gate of device 602 by operating device 602 in punch through mode (PTM) or in drain induced barrier lowering (DIBL) while device 601 is biased in at least one of a triode region and a saturation region. The converse is also true. That is, the signal on the gate of device 602 can be obtained on Cb without an attenuation of the signal on the gate of device 601 by operating device 601 in punch through mode (PTM) or in drain induced barrier lowering (DIBL) while device 602 is biased in at least one of a triode region and a saturation region. Output/readout circuitry 604 comprises bias circuitry 605 and 606 and multiplexer (MUX) 607. The signal at the gate of device 601 is read out on output conductor Ct, which is provided to bias circuitry 606. The signal at the gate of device 602 is read out on output conductor Cb, which is provided to circuitry 605. Bias circuitry 605 for Cb can be the same bias circuitry 606 for Ct or it can be different. The outputs from bias circuitry 605 and 606 are provided to a 2:1 multiplexer. The output of the multiplexer 607 is signal C_SIG. C_SIG can be an analog signal. C_SIG can be provided to ADC 913, as discussed in further detail below and with reference to FIG. 9.

Figure 7:
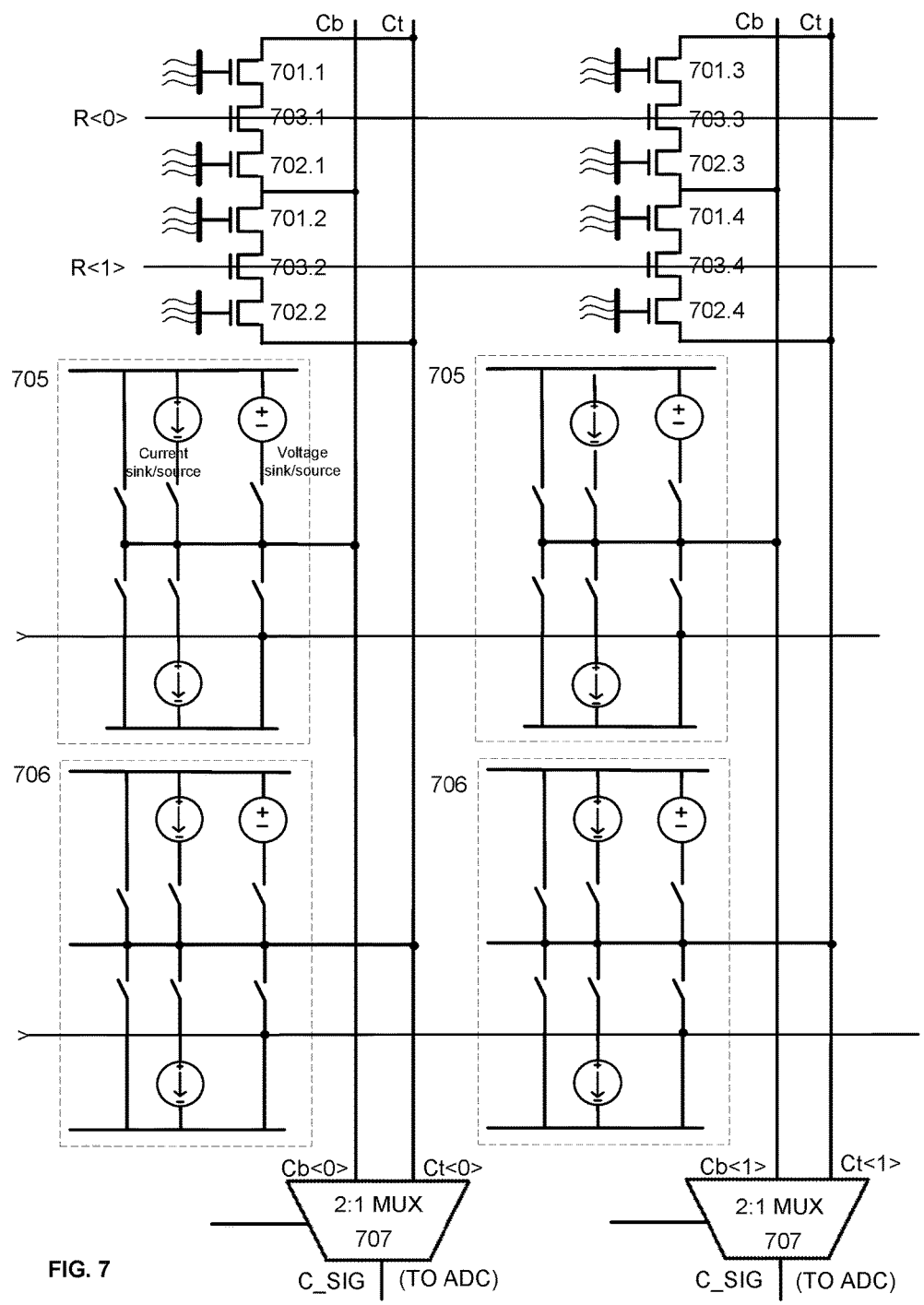
FIG. 7 illustrates a sensor array and bias circuitry according to an exemplary embodiment.
Figure 8:
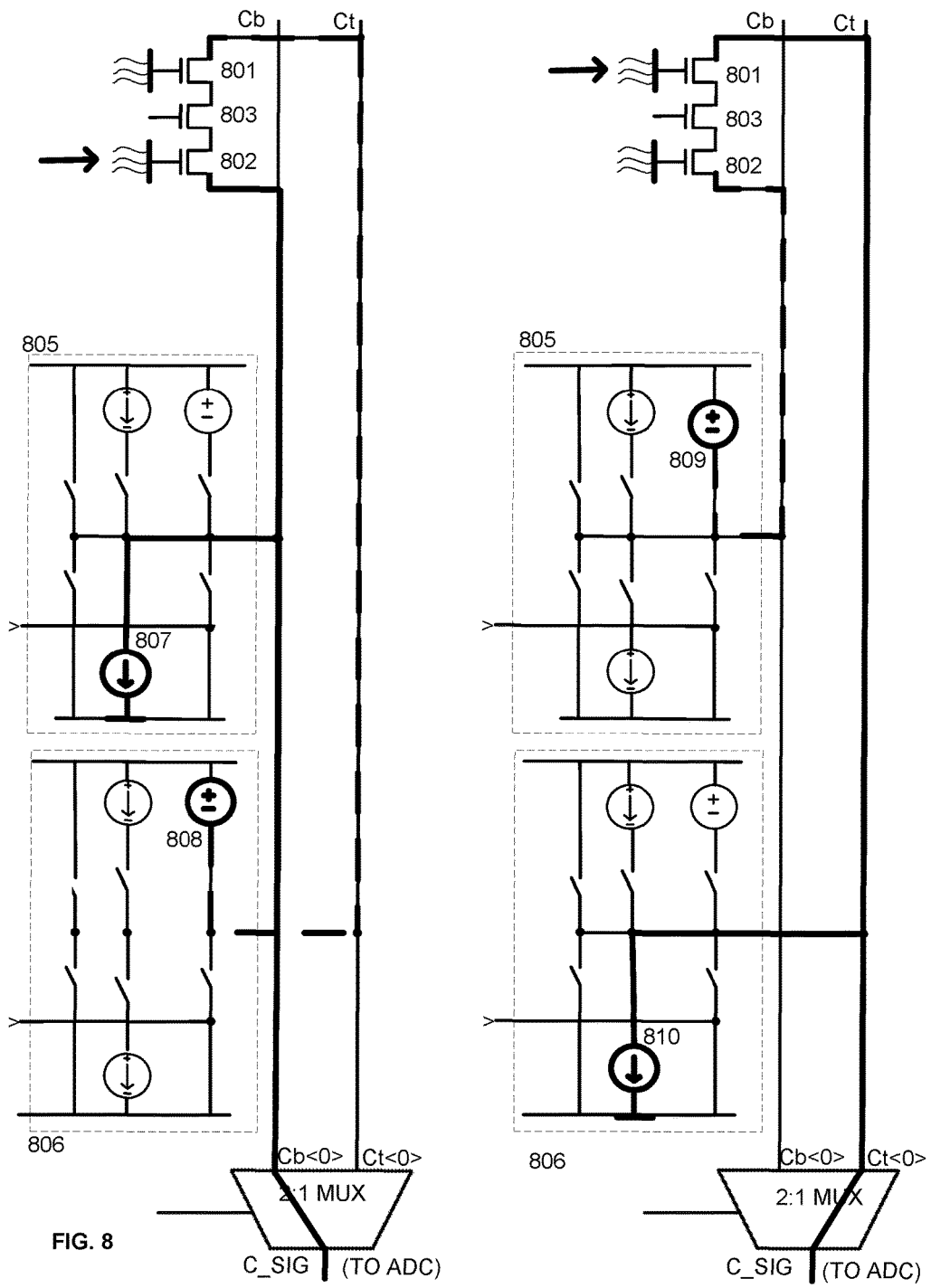
FIG. 8 illustrates a signal path for readout of a representative sensor array according to an exemplary embodiment.

FIG. 7 illustrates a sensor array and bias circuitry according to an exemplary embodiment. For simplicity, only two columns and two rows R<0> and R<1> are shown to illustrate the concept but the array can be made in various sizes as described herein. Devices 703.1, 703.2, 703.3, and 703.4 are row select devices, with row select device 703.1 and row select device 703.3 corresponding with row 0 (R<0>) and row select device 703.2 and row select device 703.4 corresponding with row 1 (R<1>). Accordingly, selecting row 0, (i.e. applying row select signal to row select devices 703.1 and device 703.3) couples the source/drain terminal of device 702.1 to column line cb<0> and to bias circuitry 705; couples the drain/source terminal of device 701.1 to column line ct<0> and to bias circuitry 706; couples the source/drain terminal of device 702.3 to column line cb<1> and to bias circuitry 705; and couples the drain/source terminal of device 701.3 to column line ct<1> and to bias circuitry 706. Bias circuitry 705 and 706 includes a plurality of current sources/sinks and (a) voltage source(s). Operation of bias circuitry 705 and 706 according to some embodiments is illustrated in FIG. 8. The output of the multiplexer 707 is signal C_SIG. C_SIG can be an analog signal. C_SIG can be provided to ADC 913, as discussed in further detail below and with reference to FIG. 9.

FIG. 8 illustrates a signal path for readout of a representative sensor array according to an exemplary embodiment. FIG. 8 illustrates two views of the same column;

the signal path for reading out the lower device (802) is shown at left and the signal path for reading out the upper device (801) is shown at right. Device 803 can be operated as a switch. Bias circuitry 805 and 806 includes a plurality of current sources/sinks and (a) voltage source(s) as shown. The solid dark line illustrates/traces the readout path for the device of interest (the device of interest indicated by the arrow) and the dashed line illustrates/traces how the device not being read is operated/biased while the device of interest is being read out. The device to be read out can be configured as a source follower. The device can be in the saturation region, for example. The select device (switch 803) can be biased into either triode or saturation region. For example, to read out device 802, saturation can be induced into device 802 with its source terminal connected to the readout current sink/source 807. One exemplary way to achieve this is to decrease the threshold of device 801 with the drain terminal connected to a high fixed potential (device 808), as illustrated at left in FIG. 8. Device 801 will have a large drain to source voltage such that the device can be effected by drain induce barrier lowering (DIBL). As a result the threshold voltage of device 801 can be decreased such that device 802 saturates. The signal from device 801 is then rejected by the output resistance of device 802.

In some embodiments, where a large drain to source voltage is present, a transistor's potential barrier from source to drain can be lowered which can require less field effect from the gate to pass the same current under lower bias. When combined with buried channel and light doping of the body of the device, for example, this can result in punch-through which can lower the barrier to the extent that little or no gate control is available. This can eliminate any signal from the device not being read (not of interest) during readout of the device of interest. Various doping schemes and gate lengths that can be used to achieve this result. In order to allow device 801 to punch-through while preserving gate control for device 802, device 803 can perform the function of drain potential bias in source follower configuration. Instead of placing device 803 into triode, device 803 can be set to saturate by using a lower voltage at the gate during select, thus lowering the drain voltage for device 802, thereby preserving gate control.

For example, to read out device 801, saturation can be induced into device 801 with its source terminal connected to the readout current sink/source 810. One exemplary way to achieve this is by decreasing the threshold of device 802 with the drain terminal connected to a high fixed potential (device 809), as illustrated at right in FIG. 8. Device 802 will have a large drain to source voltage such that the device can be effected by drain induce barrier lowering (DIBL). As a result the threshold voltage of device 802 can be decreased such that device 801 saturates. The signal from device 802 is then rejected by the output resistance of device 801. Put another way, during a first mode, a voltage within a specified operating range (i.e. the operating range of voltages within which the device is designed to operate) induced by charge on the gate of the first transistor contributes, if at all, to inducing a voltage or current on the output by an amount that is below a noise limit (or below a quantization error) of the sensing circuitry. During a second mode, a voltage within the specified operating range induced by charge on the gate of the second transistor contributes, if at all, to inducing a voltage or current on the output by an amount that is below the noise limit (or below a quantization error) of the sensing circuitry.

Figure 9:
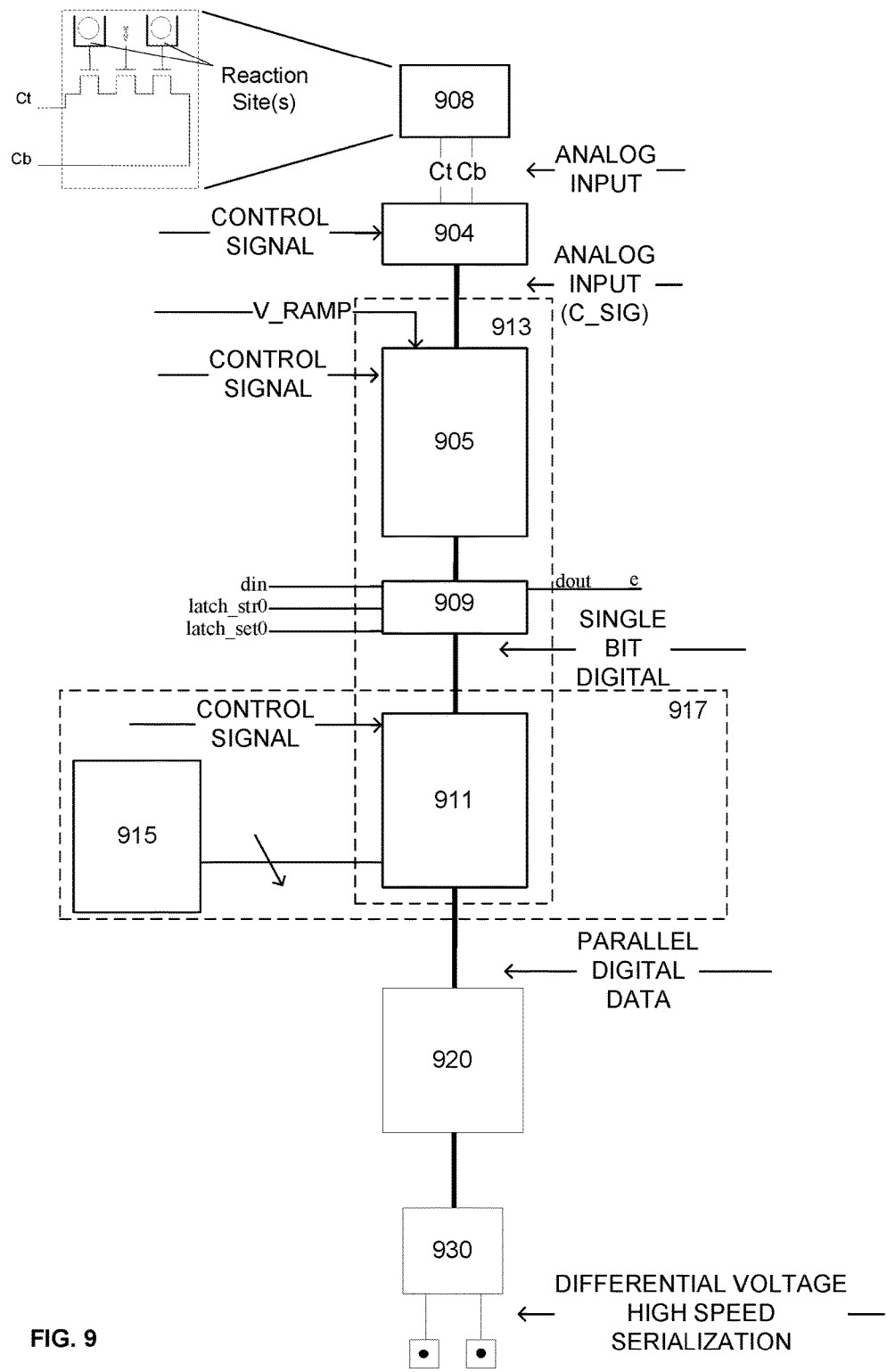
FIG. 9 illustrates a detection system according to an exemplary embodiment.

FIG. 9 illustrates a detection system according to an exemplary embodiment. In some embodiments, single input analog inputs corresponding to a biochemical reaction occurring at reaction sites (e.g. in the microwells) are converted into parallel digital data. Sensor doublet 908 can comprise two sensors in series with a switch between the sensors, as previously described. Sensor doublet 908 can operate in the same manner as sensor doublet 608 described herein with respect to FIG. 6, for example. Downstream from sensor doublet 908 is output/readout circuitry 904. Output/readout circuitry 904 includes bias circuitry and a multiplexer. Output/readout circuitry 904 receives a single analog input corresponding to a biochemical reaction occurring at a reaction site (as discussed above in the description of output/readout circuitry 604 described with respect to FIG. 6) from one of the two exemplary sensors in sensor doublet 908. Output/readout circuitry 904 also receives control signals for operating the bias circuitry and multiplexer. The bias circuitry can bias a sensor of interest to place the FET of the sensor in a known operating condition. That is, a first current is provided to place the FET in a first mode ('high' current/bandwidth) and the high bandwidth associated with the first current provides the condition which allows the circuit to settle. Optionally, once the circuit settles, a second, lower current can be provided to the FET to effectively filter noise from the sensor (i.e. fluidic noise, thermal noise, etc.) under a lower bandwidth condition in a second mode ('low' current/bandwidth). Output/readout circuitry 904 provides the conditioned voltage, still as a single analog input, to comparator 905. The comparator receives as inputs a ramp voltage (V_RAMP) and a control signal (CONTROL SIG(S) and can be a two-stage comparator which effectively reduces noise from the system and still allows for fast data readout rates by dynamically adjusting/limiting bandwidth. For example, the comparator compares the conditioned voltage from output/readout circuitry 908 with the ramp voltage and provides a single bit digital data stream as an output.

The single bit digital output data from the comparator can be provided to latch 909 and the output of the latch can interface to a register. The output of the latch may determine the sampling behavior of the gray code, discussed below. For example, latch 909 can be used to format the single bit digital data stream and transmit the formatted digital data stream to a register array 911.

The basic operation of the latch, whether early or late is:
input din;
input latch_set;
input latch_rst;
output dout;
when latch_rst=1, dout is 0.

When latch_rst=0, dout holds state until latch_set or din are triggered high.

The input gate can be a 3-input NOR. dout can be fed back to the NOR gate to hold state and to cut off current in the gating logic. The early latch can have a small propagation delay at output e. The late latch can have a long propagation delay at output 1. When the early latch fires the NAND gate inverts e and dout goes low. This can cause the reg_array to sample the gray code. When the late latch fires, the NAND gate can be evaluated false and dout drives high and rests in this state until the next reset cycle. The resulting waveform is a short pulse during which the graycode is sampled.

To run in continuous sampling mode, set
latch_rst0=0
latch_set0=1
Then run latch_rst1 and latch_set1 in normal timing fashion.

In conjunction with the latch, the comparator provides the single bit digital stream to register array 911 which provides digital parallel readout data streams. The register array can receive a control signal (CONTROL SIGNAL) and an input from gray counter 915. For example, register array 911 can convert time-shifted single bit digital data into full scale N-bit data via a gray code. The register array can capture the gray code when the digital bit is asserted. The data can be stored in a master latch. At the end of the row, the data in the master latch can be shifted to the slave latch. The register array can be configured to format the data based on an imaging configuration. For a given register address, columns can be ordered in such a way as to facilitate raster scan readout. For example, even columns can be read out together, which can cause a stacked row to be read out in correct row order. The register array comprises master and slave latches on a pre-charged output bus. For example, there may be 322 registers per bus and 96 bus lines. Select lines can be enabled with a decoder driven by a pre-decoder from Tx_align block 920. The register array can include data storage units and the register array can activate one or more of the data storage units as a function of bandwidth. Collectively, comparator 905 (and optionally, latch 909) and the register array 911 can comprise an ADC 913 (Analog to Digital Converter). Collectively, gray counter 915 and register array 911 can comprise quantizer 917. The digital parallel readout data streams from ADC 913 is provided to Tx_align 920 for alignment (data formatting) and then to transmitter 930 and to pads on the IC (see FIG. 10) where data can be sent out as differential voltage high speed serialization (for example, data can be read out at 20× the rate of input). Tx_align 920 interfaces with register array 911 with a pre-decoder and sequence timing to capture the ordered data. The data can be read out at 8 words per memory hit, for example. The data can be transferred at 20 bits per clock cycle. Tx_align 920 forms a gear box to convert incoming data widths into outgoing data widths. Tx_align 920 supports various bit depth configurations: 8,10,12b, for example. Tx_align 920 accesses memory with an addressing order dependent on both the imaging configuration as well as the register array configuration.

Figure 10:
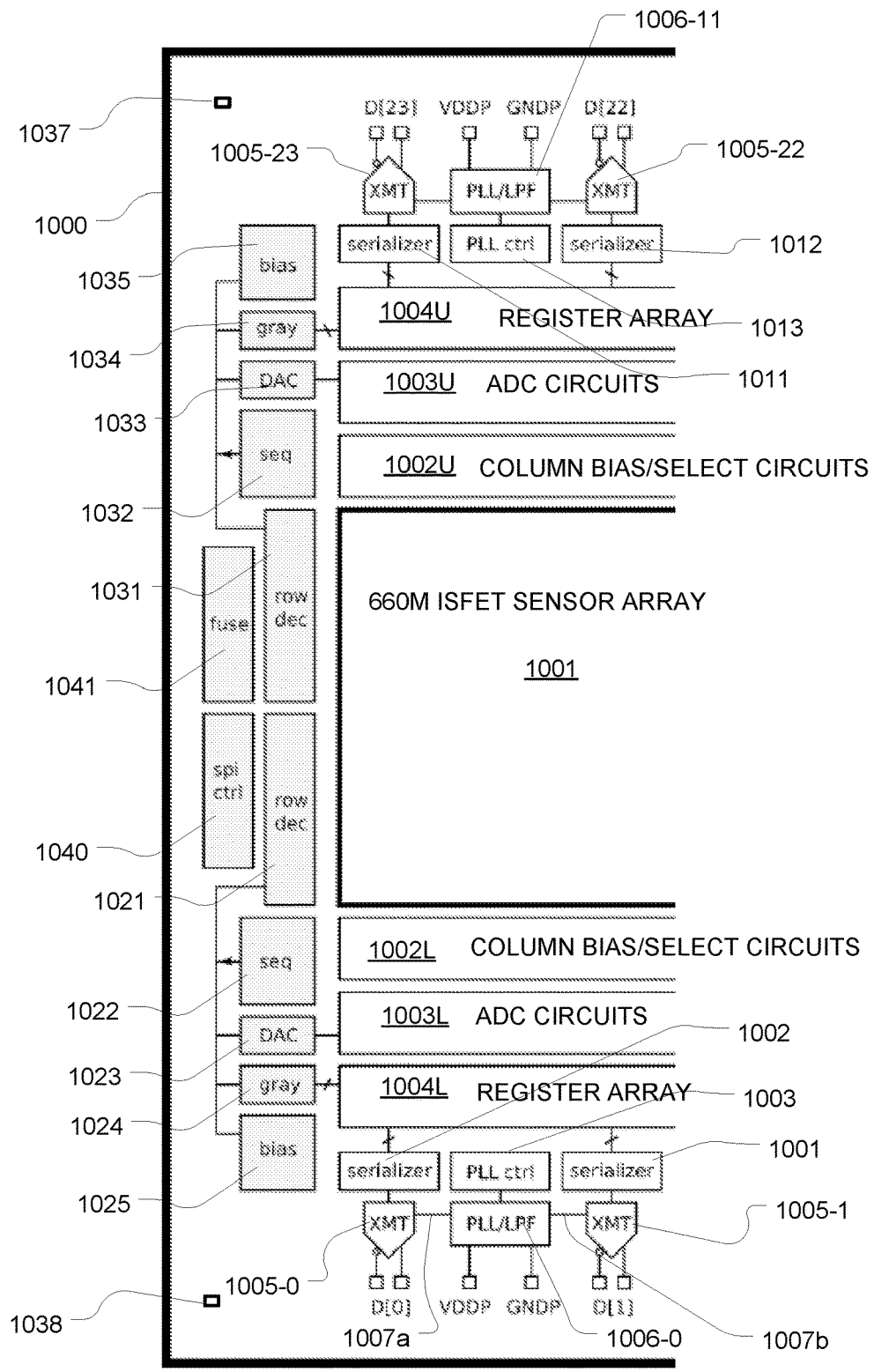
FIG. 10 illustrates a block diagram of a detection circuit according to an exemplary embodiment.

FIG. 10 is a simplified block diagram of part of the circuitry on an integrated circuit sensor array used for DNA sequencing. The exemplary integrated circuit includes a 660 megapixel ISFET sensor array 1001 on a substrate 1000. An upper set of column bias/select circuits 1002U and an upper row decoder 1031 are configured for access to an upper half of the array 1001. A lower set of column bias/select circuits 1002L and a lower row decoder 1021 are configured for access to a lower half of the array 1001. An upper set of analog-to-digital converter (ADC) circuits 1003U is coupled to the upper set of column bias/select circuits 1002U. An upper register array 1004U is coupled to the upper set of analog-to-digital converter (ADC) circuits 1003U. The upper register array 1004U is configured to provide a plurality of streams of digital data through serializers (e.g. 1011, 1012) to corresponding transmitters (e.g. 1005-23, 1005-22). Each of the transmitters is coupled to a corresponding pair (a pair for D[23], a pair for D[22]) of output pads, which in turn are connected to transmission lines (not shown). Likewise, a lower set of analog-to-digital converter circuits 1003L is coupled to the lower set of column bias/ select circuits 1002L. A lower register array 1004L is coupled to the lower set of analog-to-digital converter circuits 1003L. The lower register array 1004L is configured to provide a plurality of streams of digital data through serializers (e.g. 1001, 1002) to corresponding transmitters (e.g. 1005-0, 1005-1). Each of the transmitters is coupled to a corresponding pair (D[0], D[1]) of output pads, which in turn are connected to transmission lines (not shown). Although not illustrated, the array includes a number of reference cells, which are not coupled to the fluidics. The gates of the reference cells are coupled to a reference voltage circuit, and provide reference readings used in analysis of the data from the ISFETs that are coupled to the fluidics.

The configurations described herein support a device having a large number of gigabit per second transmitters, such as at least 20 transmitters capable of transmission at a data rate greater than 1 Gb per second, and configured in at least 10 pairs. For one example, the device includes 24 transmitters capable of transmitting data at 5 Gb per second each, or faster, supporting throughput from a high speed data source of 120 Gb per second or more. Large numbers of gigabit per second transmitters present a context in which a class of implementation problems arises which is not apparent in configurations with small numbers of transmitters. Supporting peripheral circuitry including a sequencer (seq) 1032, a digital-to-analog converter (DAC) 1033, a gray code counter (grey) 1034, and bias circuitry (bias) 1035 is coupled to the upper circuitry. Also, supporting circuitry including a sequencer (seq) 1022, a digital-to-analog converter (DAC) 1023, a gray code counter (grey) 1024, and bias circuitry (bias) 1025 is coupled to the lower circuitry. The chip includes a serial peripheral interface control block (spi ctrl) 1040 including configuration registers and providing an interface of a management bus used in configuration and control of the device, and a fuse array (fuse) 1041 used in configuration of the device. The sequencer 1022, 1032 operates the sensor array (or other data source), the peripheral circuitry and the plurality of transmitters to sample frames of data at a frame rate according an active mode and an idle mode, wherein the sequencer operates in the active mode for a first number of frames in a first time interval and in the idle mode for a second number of frames in a second time interval. The operation of the sequencer 1022, 1032 is coordinated in the sensing system with the fluidics controller, so that the first time interval overlaps with a flow of reactant solution, and the second time interval overlaps with an immediately following flow of wash solution. In one example operating technique, sequencer 1022, 1032 causes the circuitry to perform a frame sensing sequence. In a frame sensing sequence, a row of ISFETs in each of the upper and lower halves of the array is selected and biased using the column bias/select circuits 1002U/1002L so that a current that is a function of the charge in that corresponding sensor well is produced on each column line. The analog-to-digital converter circuits 1003U/1003L receive a ramp signal from the digital-to-analog converter 1033, 1023, and produce an output signal when the current on the corresponding column line matches the level of the ramp signal. The gray code counter 1024, 1034 is sampled in response to the output signal, and the results are stored in the register array 1004U/1004L. Data in the register array 1004U/1004L are assembled into packets, and applied in a plurality of digital data streams to the transmitters on the chip.

The illustrated part of the circuitry in FIG. 10 includes four transmitters out of a set of 24 transmitters on the substrate 1000. The four transmitters illustrated include a first pair of transmitters 1005-0, 1005-1, and a second pair of transmitters 1005-22, 1005-23. As shown, one phase locked loop 1006-0, including a low pass filter, is coupled to the first pair of transmitters 1005-0, 1005-1. Also, one phase locked loop 1006-11, including a low pass filter, is coupled to the second pair of transmitters 1005-22, 1005-23. The phased locked loops operate as clock multipliers, each of which produces a local transmit clock and provides the local transmit clock to the transmitter on its left and to the transmitter on its right via clock lines (e.g. 1007a, 1007b at phase locked loop 1006-0). Each phase locked loop/low pass filter, 1006-0, 1006-11, is coupled with corresponding phase locked loop control block 1003, 1013 which stores parameters used to control and calibrate phase locked loop. This pattern is repeated across the 24 transmitters on the chip, so that there are 12 phase locked loop blocks, and 24 transmitters. The transmitters are grouped into pairs which are coupled to individual phase locked loops. The phase locked loops are disposed on the substrate between the transmitters, so that the transmission distance from the phase locked loop to the transmitter using the clock produced in the phase locked loop can be small. As illustrated, each of the phase locked loops 1006-0, 1006-11 is coupled to an individual power pad VDDP and an individual ground pad GNDP. Also, the individual power pad VDDP and the individual ground pad GNDP for each phase locked loop are disposed on the chip adjacent the phase locked loop, and between the output pads for the transmitter on the left, and the output pads for the transmitter on the right in the corresponding transmitter pair.

The individual power pad VDDP and the individual ground pad GNDP are connected to an off-chip voltage supply, which can be configured with bypass capacitors and other circuitry, to create a low noise power configuration for the phase locked loop circuits, and to reduce coupling of noise between the high-frequency phase locked loop circuits and other circuits on the substrate 1000. A low-speed reference clock is distributed on the chip and connected to each of the phase locked loops. The clock multipliers in the illustrated embodiment are implemented using phase locked loops. Clock multipliers can be implemented using other circuitry as well, such as delay locked loops, phase interpolators, and combinations of phase locked loops, phase interpolators and/or delay locked loops. In this example, the integrated circuit substrate 1000 includes on-chip temperature sensors 1037, 1038, configured on each of the four corners of the chip. The temperature readings are sampled by the SPI control block 1040, and stored for access by off-chip controllers via the management bus. Also, the temperature readings are utilized by the sequencers to control power consumption and temperature on the device. In other embodiments, the temperature sensor or sensors can be configured differently. In yet other embodiments, a temperature sensor may be coupled to the microwell array structure, in addition to or in the alternative to the temperature sensor or sensors on chip.

Figure 11:
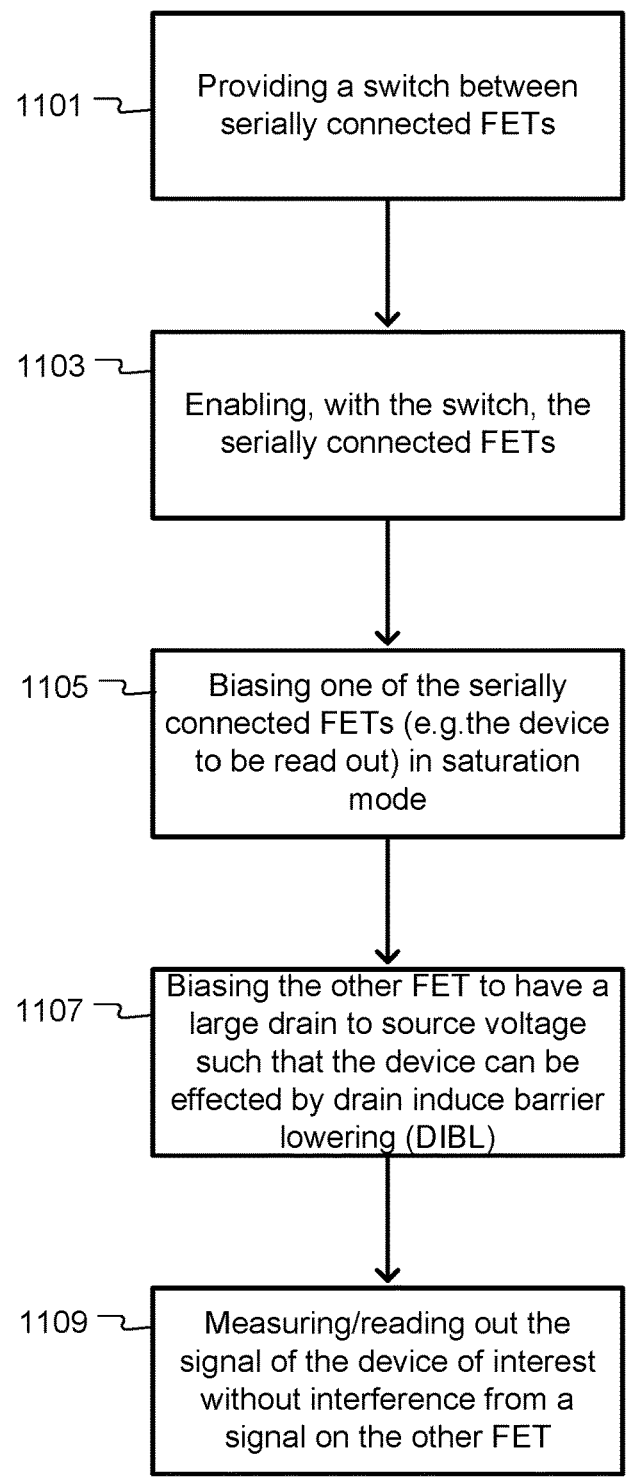
FIG. 11 is a flowchart showing a method of operating a sensor system as described herein.

FIG. 11 is a simplified flowchart showing a method of operating a sensor system as described herein. The process includes providing a switch between serially connected FETs 1101. The process includes enabling, with the switch, the serially connected FETs 1103. The process further includes biasing one of the serially connected FETs (the device to be read out) in saturation mode 1105. The process includes biasing the other FET to have a large drain to source voltage such that the device can be effected by drain induce barrier lowering (DIBL) (e.g. such that the drain terminal of the other FET is connected to a high fixed potential 1107. The process further includes measuring/reading out the signal of the device of interest without interference from a signal on the other FET 1109.

Further provided herein is a kit for performing a biological reaction. The kit may include a semiconductor device. The kit may include a chemical sensor. In some embodiments, the kit may include reagents for performing a biological reaction, including probes, primers, dyes, quantum dots, for example. In some embodiments, the kit may include a bead or particles or a solid support. In some embodiments, the kit may include a single semiconductor device. Alternatively, more than one semiconductor device may be included in the kit. In some embodiments, the kit may include a single chemical sensor. Alternatively, more than one chemical sensor may be included in the kit. In one exemplary embodiment, a semiconductor device is disclosed. The semiconductor device includes a first field effect transistor (FET) connected in series to a second FET, a third FET connected in series to the first FET and the second FET, bias circuitry coupled to the first FET and the second FET, and an output conductor coupled to a conduction terminal of the second FET, wherein the output conductor obtains an output signal from the second FET that is independent of the first FET. In some embodiments, the third FET concurrently couples the first FET and the second FET to the output conductor in response to a select signal. In some embodiments, the output signal from the second FET is independent of a voltage on a terminal of the first FET. In some embodiments, the second FET comprises a source follower. In some embodiments, the output conductor is a column bus. In some embodiments, the bias circuitry comprises at least one voltage source and at least one current sink. In some embodiments, the bias circuitry applies a voltage source to the first FET and applies a current sink to the second FET. In some embodiments, the bias circuitry concurrently applies a voltage source to the drain of the first FET and applies a current sink to the source of the second FET. In some embodiments, the output signal is dependent on the channel conductance of the second FET. In some embodiments, the first FET is operating under drain induced barrier lowering constraints and thereby is relatively insensitive to potential on its gate when the output signal is obtained from the second FET. In some embodiments, the first FET is operating under punch through mode constraints and thereby is relatively insensitive to potential on its gate when the output signal is obtained from the second FET. In some embodiments, the third FET is operated as a switch, biased in at least one of a triode region and a saturation region, and the first FET is biased at a high potential to induce drain induced barrier lowering in the first FET. In some embodiments, the output conductor is coupled to a terminal of the first FET, and the output conductor obtains a second output signal that has a magnitude from the first FET that is independent of variations of the gate voltage of the second FET. In some embodiments, the second FET is operating under at least one of drain induced barrier lowering and punch through mode constraints when the second output signal is obtained from the first FET. In some embodiments, the third FET is operated as a switch, biased in at least one of a triode region and a saturation region, and the second FET is biased at a high fixed potential to induce drain induced barrier lowering in the first FET. In some embodiments, the second FET is a chemically-sensitive field effect transistor (chemFET). In some embodiments, the chemFET is an ion sensitive field effect transistor (ISFET). In some embodiments, the output signal is based on a hydrolysis event. In some embodiments, the output signal relates to a nucleotide incorporation event detected by the second FET.

In some embodiments, the output signal relates to detection of ions by the second FET. In another exemplary embodiment, the chemical sensor includes a first field effect transistor (FET) coupled to a first electrode, a second FET coupled to a second electrode, a switch coupled to the first FET and the second FET to concurrently couple the first FET and the second FET to readout circuitry in response to a select signal, and readout circuitry coupled to a terminal of the first FET via the switch to obtain a first signal from the first FET, and coupled to a terminal of the second FET via the switch to obtain a second signal from the second FET, wherein the signal from one FET is independent of the other FET. In some embodiments, the switch is serially connected to the first FET and the second FET. In some embodiments, the switch is disposed between the first FET and the second FET. In some embodiments, the first FET is in series with the second FET. In some embodiments, the first FET is operating under at least one of drain induced barrier lowering and punch through mode constraints when the signal is obtained from the second FET. In some embodiments, the second FET is operating under at least one of drain induced barrier lowering and punch through mode constraints when the signal is obtained from the first FET. In some embodiments, the first FET detects a first reaction at a first reaction site proximate to the first electrode and the second FET detects a second reaction at a second reaction site proximate to the second electrode. In some embodiments, a current source can be coupled to the first and second FET via the switch to provide a constant drain current to the first and second FET. In some embodiments, the readout circuitry includes an output conductor. In some embodiments, the output conductor is a column bus. In some embodiments, a first output node corresponding to the terminal of the first FET and a second output node corresponding to the terminal of the second FET are concurrently coupled to the column bus in response to the select signal. In some embodiments, a first reaction site is arranged proximate to the first electrode and a second reaction site is arranged proximate to the second electrode. In some embodiments, the first FET is coupled to the first electrode via a first floating gate. In some embodiments, the second FET is coupled to the second electrode via a second floating gate. In some embodiments, the first floating gate and the second floating gate each include a plurality of conductors electrically coupled to one another and separated by dielectric layers. In some embodiments, the first electrode is sensitive to ions. In some embodiments, the second electrode is sensitive to ions. In some embodiments, the second electrode is sensitive to ions different from ions the first electrode is sensitive to. In some embodiments, the first FET comprises a source follower. In some embodiments, the second FET comprises a source follower. In some embodiments, the first signal from the first FET is independent of a voltage on a terminal of the second FET. In some embodiments, the second signal from the second FET is independent of a voltage on a terminal of the first FET. In some embodiments, the first signal relates to a chemical reaction occurring within the first reaction site and proximate to the first electrode. In some embodiments, the second signal relates to a chemical reaction occurring within the second reaction site and proximate to the second electrode. In some embodiments, the first signal relates to detection of ions by the first FET. In some embodiments, the second signal relates to detection of ions by the second FET. In some embodiments, the first signal is based on a hydrolysis event. In some embodiments, the second signal is based on a second hydrolysis event. In some embodiments, the first signal relates to a nucleotide incorporation event detected by the first FET. In some embodiments, the second signal relates to a nucleotide incorporation event detected by the second FET.

In some embodiments, a chemFET array/microfluidics hybrid structure may be used to analyze solution (s)/material(s) of interest potentially containing analytes such as nucleic acids. For example, such structures may be employed to monitor sequencing of nucleic acids. Detection and/or sequencing of analytes such as nucleic acids may be performed to determine partial or complete nucleotide sequence of a nucleic acid, to detect the presence and in some instances nature of a single nucleotide polymorphism in a nucleic acid, to determine what therapeutic regimen will be most effective to treat a subject having a particular condition as can be determined by the subject's genetic make-up, to determine and compare nucleic acid expression profiles of two or more states (e.g., comparing expression profiles of diseased and normal tissue, or comparing expression profiles of untreated tissue and tissue treated with drug, enzymes, radiation or chemical treatment), to haplotype a sample (e.g., comparing genes or variations in genes on each of the two alleles present in a human subject), to karyotype a sample (e.g., analyzing chromosomal make-up of a cell or a tissue such as an embryo, to detect gross chromosomal or other genomic abnormalities), and to genotype (e.g., analyzing one or more genetic loci to determine for example carrier status and/or species-genus relationships).

In some embodiments, the systems described herein can also be used to aid in the identification and treatment of disease. For example, the system can be used for identifying a sequence associated with a particular disease or for identifying a sequence associated with a positive response to a particular active ingredient.

In some embodiments, a method is disclosed for identifying a sequence associated with a condition comprising delivering nucleic acids from a plurality of subjects having the condition to a sequencing apparatus comprising a two-dimensional array of reaction sites, wherein each of the reaction sites is capacitively coupled to a chemFET, determining sequences of the nucleic acids from signal from said chemFETs, and identifying a common sequence between the DNA from the plurality of subjects. Preferably, the subject is a mammal, and more preferably a human. Preferably, the condition is cancer, an immunosuppressant condition, a neurological condition, or a viral infection.

In some embodiments, the systems described herein, when used for sequencing, typically involve a chemFET array supporting discrete sites, the chemFETs being coupled to an interface capable of executing logic that converts the signals from the chemFETs into sequencing information. In some embodiments, the system described herein encompasses logic (preferably computer executable logic) for polymer sequencing, comprising logic for determining ion pulses associated with an ionic interaction with a PPi or a dNTP or both. Typically, the logic converts characteristic(s) of the ion pulses into polymer sequencing information. In some embodiments, the system described herein encompasses logic (preferably computer executable logic) comprising logic for determining a sequence of a nucleic acid template based on time between ion pulses or a characteristic of a single ion pulse. The logic may optionally further comprise logic for determining spatial location of the ion pulse on an array of chemFETs. In some embodiments, the system described herein encompasses logic (preferably computer executable logic) comprising logic for determining a sequence of a nucleic acid template based on a duration of time it takes for a particular dNTP to be utilized in a sequencing reaction. Typically, the logic receives signal from one or more chemFETs. Preferably, the sequence is displayed in substantially real time. In some embodiments, the system described herein encompasses logic (preferably computer executable logic) for processing ion pulses from an array of chemFETs to determine the sequence of a polymer of interest. The logic may optionally further comprise logic for file management, file storage, and visualization. The logic may also optionally further comprise logic for converting the ion pulses into nucleotide sequences. Preferably, the sequence is displayed in substantially real time. The sequencing information obtained from the system may be delivered to a handheld computing device, such as a personal digital assistant. Thus, in one embodiment, the system described herein encompasses logic for displaying a complete genome of an organism on a handheld computing device. Also encompassed is the use of logic adapted for sending data from a chemFET array to a hand held computing device. Any of such logic may be computer-implemented.

Development of the very large chemFET arrays and systems provides considerable advantages to a wide assortment of applications beyond the particular DNA sequencing process described above. For example, performing dPCR on the chemFET array is contemplated. Further, protein arrays used in combination with the chemFET arrays as described herein are also contemplated. Protein arrays comprise proteins or peptides or other amino acid comprising biological moiety bound to a planar surface in an organized and predetermined manner. Such proteins include but are not limited to enzymes, antibodies and antibody fragments or antibody mimics (e.g., single chain antibodies).

A chemFET-based array may also be used to explore various protein/nucleic acid interactions. For example, RNA/protein binding may be investigated by lysing cells and capturing the RNA (with associated proteins) on oligonucleotides immobilized on the chemFET array. Enzyme conjugated antibodies may then be bound to protein antigen and nonspecific interactions can be washed away. Specific antibodies may be employed against translational machinery and 80S, 40S, 43S, or 48S RNA regions. Antibodies may also be used against RNA binding proteins, or conjugated to enzymes that produce ionic products when presented with nonionic substrates (for example NADPH to NADP+, NADH to NAD+, and possibly H2O2 or Glutathione). These antibodies can be combined for multiplexing.

In some embodiments, the use of chemFET arrays, as described herein or in another manner, for use in vivo is contemplated. Such an array may be introduced into a subject (e.g., in the brain or other region that is subject to ion flux) and then analyzed for changes based on the status of the subject.

In some embodiments, a chemFET array may be directly implanted into a test environment and used to monitor the presence and amount of specific molecules of interest. Some such applications include environmental testing for specific toxins and important elements, or direct implantation of the device into the body of a subject, providing a 3D image of the concentration of specific molecules within the tissue.

Note that not all of the activities described herein in the general description or the examples are required, that a portion of a specific activity cannot be required, and that one or more further activities can be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but can include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present). The designation of source or drain is one of convention/convenience as used above as these labels depend on how a given device is being operated and how (a) given device(s) is/are fabricated.

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described herein with regard to specific embodiments. However, the benefits, advantages, solutions to problems, and any feature(s) that can cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any subcombination. Further, references to values stated in ranges include each and every value within that range.

What is claimed is:

1. A semiconductor device, comprising:
   a first field effect transistor (FET), the first FET having a first electrode proximate to a first reaction site;
   a second FET connected in series to the first FET, the second FET having a second electrode proximate to a second reaction site;
   a select transistor connected in series to the first FET and the second FET, wherein the select transistor concurrently couples the first FET to a first output conductor and the second FET to a second output conductor in response to a select signal; and
   bias circuitry coupled to the first FET and the second FET, wherein the bias circuitry is configured to apply a voltage to one of either the first FET or the second FET, and to concurrently apply a current sink to the other of the first or the second FET.

2. The device of claim 1, wherein an output signal from the other of the first FET obtained on the first output conductor or the second FET obtained on the second output conductor is independent of the voltage applied to one of either the first FET or the second FET.

3. The device of claim 1, wherein the bias circuitry comprises at least one voltage source and at least one current sink.

4. The device of claim 1, wherein the bias circuitry is configured to operate one of either the first FET or the second FET under at least one of drain induced barrier lowering or punch through mode constraints.

5. The device of claim 4, wherein when one of either the first FET or the second FET operates under drain induced barrier lowering or punch through mode constraints, an output signal is obtained from the other of the first FET or the second FET.

6. The device of claim 1, wherein the select transistor is biased in at least one of a triode region and a saturation region.

7. The device of claim 1, wherein the first FET and the second FET are chemically-sensitive field effect transistors (chemFETs).

8. The device of claim 1, wherein the first FET and the second FET are ion-sensitive field effect transistors (ISFETs).

9. The device of claim 8, wherein the ISFETS are sensitive to hydrogen ions.

10. The device of claim 1, wherein the select transistor is a FET.

11. The device of claim 1, wherein the first electrode proximate to the first reaction site is coupled to a floating gate structure.

12. The device of claim 1, wherein the second electrode proximate to the second reaction site is coupled to a floating gate structure.

* * * * *